(12) United States Patent
Bolognia et al.

(10) Patent No.: US 12,196,705 B2
(45) Date of Patent: Jan. 14, 2025

(54) FLUID SENSOR MODULE

(71) Applicant: Analog Devices International Unlimited Company, Limerick (IE)

(72) Inventors: David Frank Bolognia, Charlestown, MA (US); Jiawen Bai, Brighton, MA (US); Youri Victorovitch Ponomarev, Rotselaar (BE); Claire E. Leahy, Listowel (IE); Liam Riordan, Patrickswell (IE); Aileen Anne Cleary, Somerville, MA (US)

(73) Assignee: Analog Devices International Unlimited Company, Limerick (IE)

( * ) Notice: Subject to any disclaimer, the term of this patent is extended or adjusted under 35 U.S.C. 154(b) by 0 days.

(21) Appl. No.: 17/654,177

(22) Filed: Mar. 9, 2022

(65) Prior Publication Data

US 2022/0291165 A1 Sep. 15, 2022

Related U.S. Application Data

(60) Provisional application No. 63/158,788, filed on Mar. 9, 2021.

(51) Int. Cl.
*G01N 27/416* (2006.01)
*A61M 1/16* (2006.01)
*A61M 39/22* (2006.01)

(52) U.S. Cl.
CPC ....... *G01N 27/4163* (2013.01); *A61M 1/1619* (2014.02); *A61M 39/223* (2013.01); *A61M 2205/702* (2013.01)

(58) Field of Classification Search
None
See application file for complete search history.

(56) References Cited

U.S. PATENT DOCUMENTS

| 9,239,322 | B2 * | 1/2016 | Mahoney | G01N 33/0016 |
| 10,830,692 | B2 * | 11/2020 | Wang | G01N 21/314 |
| 2004/0163970 | A1 | 8/2004 | Sin et al. | |
| 2009/0156922 | A1 | 6/2009 | Goldberger et al. | |
| 2010/0168546 | A1 | 7/2010 | Kamath et al. | |
| 2011/0077480 | A1 | 3/2011 | Bloom et al. | |

(Continued)

FOREIGN PATENT DOCUMENTS

| CN | 106716137 A | 5/2017 |
| EP | 226593 B1 * | 1/1992 |

(Continued)

OTHER PUBLICATIONS

International Search Report and Written Opinion in PCT/EP2022/082114, dated Feb. 7, 2023 in 8 pages.

(Continued)

*Primary Examiner* — Daniel S Larkin
(74) *Attorney, Agent, or Firm* — Knobbe, Martens, Olson & Bear, LLP

(57) ABSTRACT

A fluid sensor device can include a housing having an inlet and an outlet. The housing can have a fluid reservoir, a sensing assembly, a plunger, a valve, and a plurality of channels. The fluid sensor module can be used to sense constituents in a sample fluid (e.g. patient's blood or dialysate) during a treatment process, such as kidney dialysis procedures. The fluid sensor module can be connected in-line to a medical device to sense the sample fluid.

20 Claims, 22 Drawing Sheets

(56) References Cited

U.S. PATENT DOCUMENTS

| | | |
|---|---|---|
| 2020/0182891 A1 | 6/2020 | Di Tullio et al. |
| 2023/0149608 A1 | 5/2023 | Ponomarev et al. |
| 2023/0152189 A1 | 5/2023 | Ponomarev et al. |
| 2024/0035933 A1 | 2/2024 | Bolognia et al. |

FOREIGN PATENT DOCUMENTS

| | | | |
|---|---|---|---|
| WO | WO-2020176663 A1 * | 9/2020 | .......... A61M 1/1609 |
| WO | WO 2023/088954 A1 | 5/2023 | |

OTHER PUBLICATIONS

International Preliminary Report on Patentability in PCT/EP2022/082114, dated May 2, 2024 in 6 pages.

* cited by examiner

Calibration Position

Sensing Position

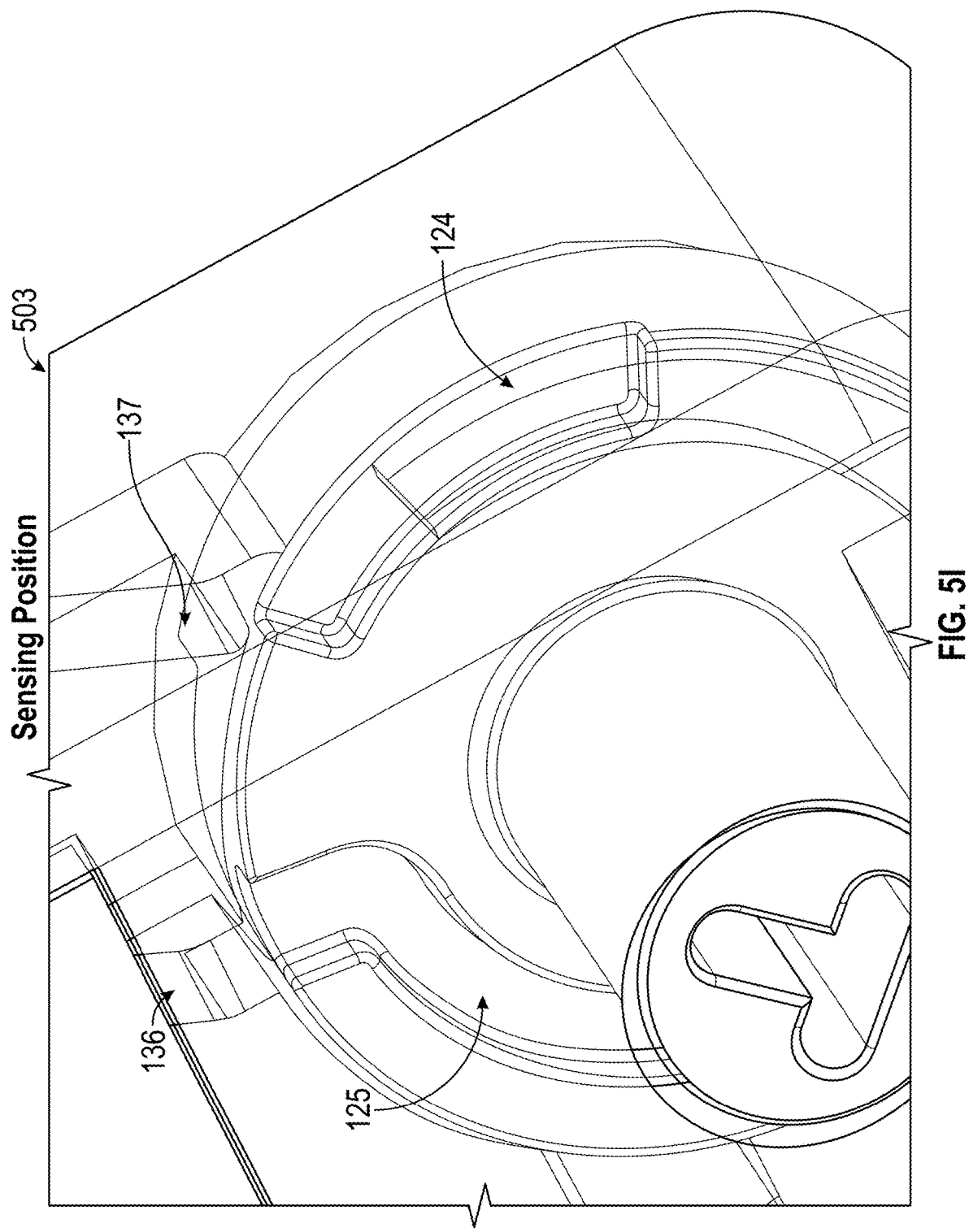

Fill Position

FLUID SENSOR MODULE

CROSS-REFERENCE TO RELATED APPLICATIONS

The present application claims priority to U.S. Provisional Patent Application No. 63/158,788, filed Mar. 9, 2021, and titled "FLUID SENSOR MODULE," the entirety of which is hereby incorporated herein by reference.

BACKGROUND

Field

The field relates to a fluid sensor module.

Description of the Related Art

Many medical treatment procedures are performed in a hospital or outpatient facility, such that the patient must typically be admitted to the facility to undergo treatment. Treatment procedures, such as kidney dialysis procedures, may need to be performed on a regular basis, which can be inconvenient, time-consuming, and economically costly to the patient and the clinician. Enabling such treatment procedures to be performed in the patient's home can advantageously improve the convenience, efficiency, and affordability of the procedures.

SUMMARY

In one embodiment, a fluid sensor module comprises: a sensing assembly; a fluid pathway configured to transfer a sample fluid to be in fluid communication with the sensing assembly; and a valve movable between a sensing position in which the sample fluid is transferred along the fluid pathway and a calibration position in which a calibration fluid is transferred from a calibration fluid reservoir along the fluid pathway.

In some embodiments, the fluid sensor module can comprise a housing, the sensing assembly coupled to or formed with the housing. In some embodiments, the fluid sensor module can comprise a fluid inlet to transfer the sample fluid into the housing and a fluid outlet to transfer the sample fluid out of the housing, wherein when the valve is in the sensing position, the sample fluid is conveyed from the fluid inlet, along the fluid pathway, and through the outlet. In some embodiments, when the valve is in the calibration position, the calibration fluid is conveyed from the calibration fluid reservoir, along the fluid pathway, and through the outlet. In some embodiments, when the valve is in the calibration position, the sample fluid is conveyed from the fluid inlet to the fluid outlet so as to bypass the fluid pathway. In some embodiments, the valve has a bypass position in which the fluid inlet is directly connected to the fluid outlet such that the sample fluid is conveyed from the fluid inlet to the fluid outlet so as to bypass the fluid pathway, the valve in the bypass position blocking the calibration fluid from entering the fluid pathway. In some embodiments, the valve has a fill position in which the fluid inlet is directly connected to the calibration fluid reservoir to transfer the calibration fluid from an external source to the calibration fluid reservoir. In some embodiments, when the valve is in the sensing position, a portion of the sample fluid flows directly between the fluid inlet and the fluid outlet so as to bypass the fluid pathway. In some embodiments, when the valve is in the sensing position, an entirety of the sample fluid flows along the fluid pathway such that substantially no portion of the sample fluid bypasses the fluid pathway. In some embodiments, the fluid sensor module can comprise a plunger coupled to the housing in the calibration fluid reservoir, the plunger movable to drive the calibration fluid along a calibration fluid pathway to the valve. In some embodiments the plunger is rotatable relative to the housing, the plunger having a plunger connector configured to operably connect to a plunger motor. In some embodiments, the valve is rotatable relative to the housing, the valve having a valve connector configured to operably connect to a valve motor. In some embodiments, the sensing assembly comprises a functionalized electrode configured to, in response to interacting with the sample fluid, transmit a signal indicative of a constituent component of the sample fluid. In some embodiments, the sensing assembly comprises a plurality of functionalized electrodes and a plurality of I/O pads electrically connected to the functionalized electrodes, each functionalized electrode of the plurality of functionalized electrodes configured to, in response to interacting with the sample fluid, transmit a corresponding signal to a corresponding I/O pad indicative of a constituent component of the sample fluid. In some embodiments, the fluid pathway passes over the functionalized electrode to provide fluid communication between the functionalized electrode and the sample fluid.

In some embodiments, a fluid sensing system can include the fluid sensor module and a reader, the fluid sensor module configured to electrically and mechanically connect to the reader. In some embodiments, the reader comprises a plurality of leads configured to electrically connect to corresponding I/O pads of the fluid sensor module, a first motor configured to mechanically connect to a plunger in the calibration reservoir, and a second motor configured to mechanically connect to the valve.

In some embodiments, a medical device includes a treatment system configured to treat a patient; and the fluid sensor module in fluid communication with the treatment system. In some embodiments, the treatment system comprises a hemodialysis machine to treat blood of the patient, the sample fluid comprising the blood. In some embodiments, the treatment system comprises a peritoneal dialysis machine to pump dialysate through the patient, the sample fluid comprising the dialysate.

In another embodiment, a fluid sensor module comprises: a housing; a fluid inlet configured to transfer a sample fluid into the housing; a sensing assembly coupled to or formed with the housing; a fluid pathway configured to transfer the sample fluid to be in fluid communication with the sensing assembly; a fluid outlet configured to transfer the sample fluid out of the housing; and a valve in fluid communication with the fluid inlet, the fluid pathway, and the fluid outlet. The valve can have a sensing position in which the sample fluid is conveyed from the fluid inlet, along the fluid pathway, and through the outlet. The valve can have a calibration position in which a calibration fluid is conveyed from a calibration fluid reservoir, along the fluid pathway, and through the outlet.

In some embodiments, when the valve is in the calibration position, the sample fluid is conveyed from the fluid inlet to the fluid outlet so as to bypass the fluid pathway. In some embodiments, the valve has a bypass position in which the fluid inlet is directly connected to the fluid outlet such that the sample fluid is conveyed from the fluid inlet to the fluid outlet so as to bypass the fluid pathway, the valve in the bypass position blocking the calibration fluid from entering the fluid pathway. In some embodiments, the valve has a fill position in which the fluid inlet is directly connected to the calibration fluid reservoir to transfer the calibration fluid from an external source to the calibration fluid reservoir. In some embodiments, when the valve is in the sensing position, a portion of the sample fluid flows directly between the fluid inlet and the fluid outlet so as to bypass the fluid pathway. In some embodiments, when the valve is in the sensing position, an entirety of the sample fluid flows along the fluid pathway such that substantially no portion of the sample fluid bypasses the fluid pathway. In some embodiments, the fluid sensor module can comprise a plunger coupled to the housing in the calibration fluid reservoir, the plunger movable to drive the calibration fluid along a calibration fluid pathway to the valve. In some embodiments, the plunger is rotatable relative to the housing, the plunger having a plunger connector configured to operably connect to a plunger motor. In some embodiments, the valve is rotatable relative to the housing, the valve having a valve connector configured to operably connect to a valve motor. In some embodiments, the sensing assembly comprises a functionalized electrode configured to, in response to interacting with the sample fluid, transmit a signal indicative of a constituent component of the sample fluid. In some embodiments, the sensing assembly comprises a plurality of functionalized electrodes and a plurality of I/O pads electrically connected to the functionalized electrodes, each functionalized electrode of the plurality of functionalized electrodes configured to, in response to interacting with the sample fluid, transmit a corresponding signal to a corresponding I/O pad indicative of a constituent component of the sample fluid. In some embodiments, the fluid pathway passes over the functionalized electrode to provide fluid communication between the functionalized electrode and the sample fluid.

In some embodiments, a fluid sensing system includes the fluid sensor module and a reader, the fluid sensor module configured to electrically and mechanically connect to the reader. In some embodiments, the reader comprises a plurality of leads configured to electrically connect to corresponding I/O pads of the fluid sensor module, a first motor configured to mechanically connect to a plunger in the calibration reservoir, and a second motor configured to mechanically connect to the valve.

In some embodiments, a medical device includes a treatment system configured to treat a patient; and the fluid sensor module in fluid communication with the treatment system between the treatment system and the patient. In some embodiments, the treatment system comprises a hemodialysis machine to treat blood of the patient. In some embodiments, the treatment system comprises a peritoneal dialysis machine to pump dialysate through the patient.

In another embodiment, a multi-port fluid valve for a fluid sensor module is disclosed. The valve can include: a valve body configured to be in operable communication with a first inlet channel through which a sample fluid enters the fluid sensor module, a second outlet channel through which fluid exits the fluid sensor module, a third calibration channel through which a calibration fluid flows, a fourth sample entry channel to transfer the sample fluid to be in fluid communication with a sensing assembly, and a fifth sample exit channel to transfer the sample fluid away from the sensing assembly. The valve can have a sensing mode in which the first inlet channel and the fourth sample entry channel are connected, the fifth sample exit channel and the second outlet channel are connected, and the third calibration channel is closed. The valve can have a calibration mode in which the first inlet channel and the second outlet channel are connected, the third calibration channel and the fourth sample entry channel are connected, and the fifth sample exit channel and the second outlet channel are connected.

In some embodiments, in the sensing mode, the first inlet channel and the second outlet channel are partially connected to provide a regulated flow rate therebetween. In some embodiments, the valve has a bypass mode in which the first inlet channel and the second outlet channel are connected, and in which the third calibration channel, the fourth sample entry channel, and the fifth sample exit channel are closed. In some embodiments, the valve has a filling mode in which the first inlet channel is connected to the third calibration channel, and in which the second outlet channel, the fourth sample entry channel, and the fifth sample exit channel are closed. In some embodiments, the valve body comprises a through recess formed vertically through a head of the valve body, the through recess extending circumferentially along the valve body at a first angle. In some embodiments, the valve body comprises an upper partial recess formed partially through the head of the valve body, the upper partial recess extending circumferentially along the valve body at a second angle. In some embodiments, the valve body comprises a first lower partial recess formed partially through the head of the valve body, the first lower partial recess extending circumferentially along the valve body at a third angle. In some embodiments, the valve body comprises a second lower partial recess formed partially through the head of the valve body, the second lower partial recess extending circumferentially along the valve body at a fourth angle. In some embodiments, the second lower partial recess partially circumferentially overlaps with the upper partial recess. In some embodiments, the second lower partial recess comprises an angled or curved recess having a first portion extending from the through recess circumferentially along the valve body and a second portion extending radially outward from the first portion. In some embodiments, in the bypass mode, in the calibration mode, and in the sensing mode, the through recess provides fluid communication between the first inlet channel and the second outlet channel. In some embodiments, in the calibration mode, the upper partial recess provides fluid communication between the third calibration channel and the fourth sample entry channel. In some embodiments, in the calibration mode, the second lower partial recess provide fluid communication between the fifth sample exit channel and the second outlet channel. In some embodiments, in the sensing mode, the through recess permits a portion of the sample fluid to flow from the first inlet channel to the second outlet channel. In some embodiments, in the sensing mode, the second lower partial recess provides fluid communication between the first inlet channel and the fourth sample entry channel. In some embodiments, in the sensing mode, the first lower partial recess provides fluid communication between the fifth sample exit channel and the second outlet channel. In some embodiments, in the filling mode, the through recess provides fluid communication between the first inlet channel and the third calibration channel.

In another embodiment, a fluid sensor module can include: a housing; a fluid inlet configured to transfer a sample fluid into the housing; a sensing assembly coupled to or formed with the housing, the sensing assembly comprising a functionalized electrode configured to, in response to interacting with the sample fluid during a sensing mode, transmit a signal indicative of a constituent component of the sample fluid; a fluid pathway configured to transfer the fluid to be in fluid communication with the functionalized electrode; a calibration reservoir in the housing to hold a calibration fluid; a plunger in the calibration reservoir, the plunger configured to drive the calibration fluid along the fluid pathway during a calibration mode; and a valve movable among a bypass position in which the sample fluid bypasses the fluid pathway during a bypass mode, a sensing position in which the sample fluid is transferred along the fluid pathway during the sensing mode, a calibration position in which the calibration fluid is driven by the plunger from the calibration fluid reservoir along the fluid pathway to purge the fluid pathway in the calibration mode, and a fill position in which the calibration fluid is supplied to the calibration reservoir in a fill mode.

In some embodiments, the sensing assembly comprises a plurality of functionalized electrodes and a plurality of I/O pads electrically connected to the functionalized electrodes, each functionalized electrode of the plurality of functionalized electrodes configured to, in response to interacting with the sample fluid in the sensing mode, transmit a corresponding signal to a corresponding I/O pad indicative of a constituent component of the sample fluid.

In some embodiments, a fluid sensing system can include the fluid sensor module and a reader, the fluid sensor module configured to electrically and mechanically connect to the reader. In some embodiments, the reader comprises a plurality of leads configured to electrically connect to corresponding I/O pads of the fluid sensor module, a first motor configured to mechanically connect to a plunger in the calibration reservoir, and a second motor configured to mechanically connect to the valve.

In another embodiment, a fluid sensing system can include a fluid sensor module comprising: a fluid inlet and a fluid outlet, the fluid inlet and the fluid outlet configured to fluidly communicate with a medical device; an I/O pad in electrical communication with a functionalized electrode, the functionalized electrode configured to transmit to the I/O pad a signal indicative of a constituent component of a sample fluid to which the functionalized electrode is exposed in a sensing mode of the fluid sensor module; a calibration fluid reservoir to hold a calibration fluid; a plunger to drive the calibration fluid across the functionalized electrode in a calibration mode of the fluid sensor module, the plunger having a plunger connector; and a valve having a sensing position that places the fluid sensor module in the sensing mode and a calibration position that places the fluid sensor module in the calibration mode, the valve having a valve connector. The fluid sensing system can include a reader configured to removably connect to the fluid sensor module. The reader can include: a lead configured to electrically connect to the I/O pad of the fluid sensor module; a first motor configured to mechanically engage with the plunger connector to move the plunger in the calibration mode; and a second motor configured to mechanically engage with the valve connector to move the valve to switch modes of the fluid sensor module.

In some embodiments, the fluid sensor module comprises a plurality of I/O pads electrically connected to a corresponding plurality of functionalized electrodes, each functionalized electrode of the plurality of functionalized electrodes configured to, in response to interacting with the sample fluid in the sensing mode, transmit a corresponding signal to a corresponding I/O pad indicative of a constituent component of the sample fluid. In some embodiments, the valve has a bypass position in which the sample fluid bypasses the fluid pathway during a bypass mode and a fill position in which the calibration fluid is supplied to the calibration reservoir in a fill mode. In some embodiments, the first motor is configured to rotate the plunger by a predetermined angle during the calibration mode.

In another embodiment, a fluid sensor assembly can include: a housing that at least partially defines a calibration reservoir to hold a calibration fluid; a calibration channel to deliver the calibration fluid to a sensing assembly; and a plunger rotatably coupled to the housing, the plunger configured to rotate relative to the housing to drive the calibration fluid into the calibration channel.

In some embodiments, the plunger is configured to rotate about a pivot axis disposed in a first region of the housing, and wherein the calibration channel is disposed in a second region laterally offset from the first region along a lateral direction of the housing, the pivot axis perpendicular to the lateral direction. In some embodiments, the first region comprises a corner of the housing. In some embodiments, the plunger comprises a seal about its periphery, the seal configured to seal against the housing. In some embodiments, the plunger comprises a two-shot molded body comprising a plastic body and a rubber seal molded about the plastic body.

In various embodiments, the fluid sensor module can comprise a waste container, the valve configured to direct used calibration fluid to the waste container. In some embodiments, the waste container is disposed over the calibration fluid reservoir and separated from the calibration fluid reservoir by a partition. In some embodiments, the waste container is laterally adjacent the calibration fluid reservoir and separated from the calibration fluid reservoir by a partition.

In yet another embodiment, a method of sensing fluid can comprise rotating a valve body to switch between a plurality of operating modes, the plurality of operating modes comprising a sensing mode and a calibration mode, sensing one or more constituent component of a sample fluid in the sensing mode using one or more functionalized electrodes, and calibrating the one or more functionalized electrodes by driving a calibration fluid over the one or more functionalized electrodes in the calibration mode.

In some embodiments, the method of sensing fluid can further comprise rotating the valve body to switch to a bypass mode, and directing the sample fluid to be conveyed from a fluid inlet to a fluid outlet, bypassing the fluid pathway.

In some embodiments, the method of sensing fluid can further comprise rotating the valve body to switch to a filling mode, and driving the calibration fluid through the fluid inlet and to a calibration fluid reservoir.

BRIEF DESCRIPTION OF THE DRAWINGS

FIG. 5I is a magnified bottom perspective internal view of the fluid sensor module if FIG. 1A in a sensing position.

DETAILED DESCRIPTION

Figure 1B:
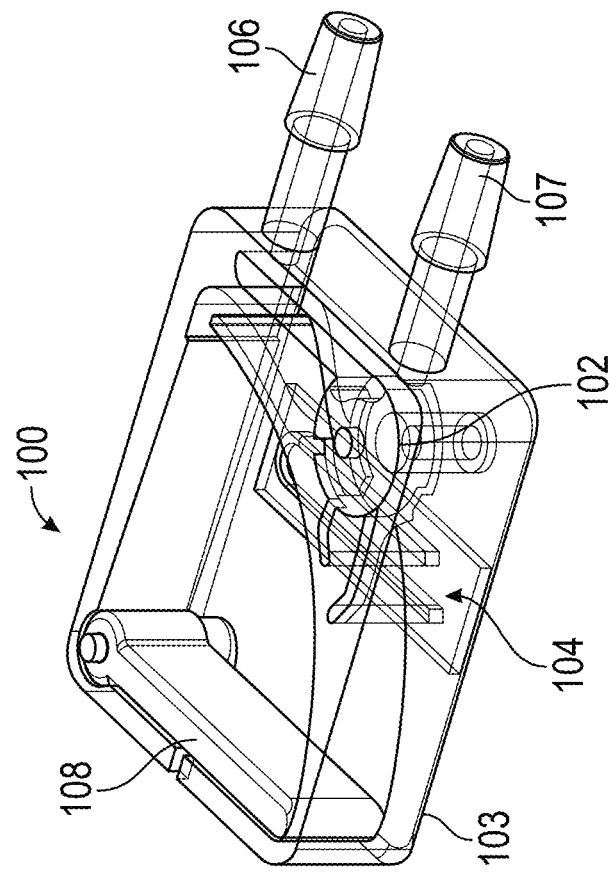
FIG. 1B is an internal view of the fluid sensor module in FIG. 1A.
Figure 1A:
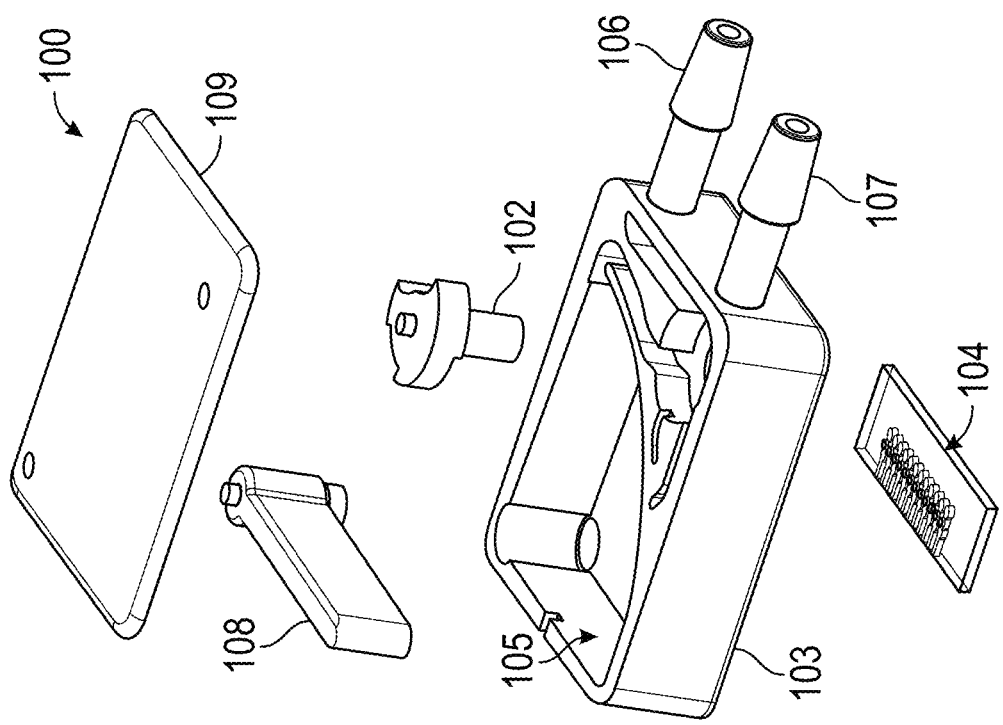
FIG. 1A is an exploded top perspective view of a fluid sensor module.

Various embodiments relate herein to a fluid sensor module configured to connect in-line to a medical device, such as a dialysis treatment system. For example, in kidney hemodialysis systems, blood can be transferred from the patient, through the dialysis treatment system, and back into the patient, to treat the patient's blood. In a peritoneal dialysis (PD) system, the treatment system can pump dialysate in a circulation through the abdominal cavity. During a treatment procedure, it can be important to monitor the composition of constituent materials in a sample fluid such as a treatment fluid (e.g., dialysate) and/or the patient's blood, such as creatinine, potassium, sodium, or any other constituent material that should be monitored. The fluid sensor module can be placed upstream or downstream of the treatment system to monitor the constituent materials.

Beneficially, the fluid sensor module can be sized and configured to be used at home by the patient, or in a clinical setting such as a hospital or clinic. For example, the fluid inlet and outlet can connect to the treatment system by way of a quick connection such as a luer lock or other fluid coupling. The fluid sensor module can mechanically and electrically connect to a reader which can both control the operation of the fluid sensor module and receive and transmit sensing information from the fluid sensor module.

The sensor module can comprise a sensing assembly including a plurality of functionalized electrodes (e.g., twelve electrodes in the illustrated embodiment) that, when exposed to the sample fluid, transmit a signal indicative of a particular constituent component of the sample fluid. A fluid pathway can extend and circulate over the functionalized electrodes to expose the functionalized electrodes to the sample fluid. As shown, the fluid pathway can comprise a curved pathway formed in the housing to convey the sample fluid (and calibration fluid) over the electrodes. The electrodes can electrically connect to corresponding I/O pads.

FIGS. 1A-5K shows one embodiment of a fluid sensor module. The fluid sensor module 100 shown in FIGS. 1A-1B can include a lid 109 enclosing a housing 103. The housing 103 can include a fluid inlet 106 and a fluid outlet 107 configured to fluidly connect to a treatment system of the medical device and convey liquid from and back to the treatment system. The module 100 can include a calibration fluid reservoir 105, a plunger 108, and a valve 102 inside the housing 103 of the fluid sensor module 100. A sensing assembly 104 can be provided at (e.g., attached to) the bottom of the fluid sensor module.

Figures 2A, 2B:
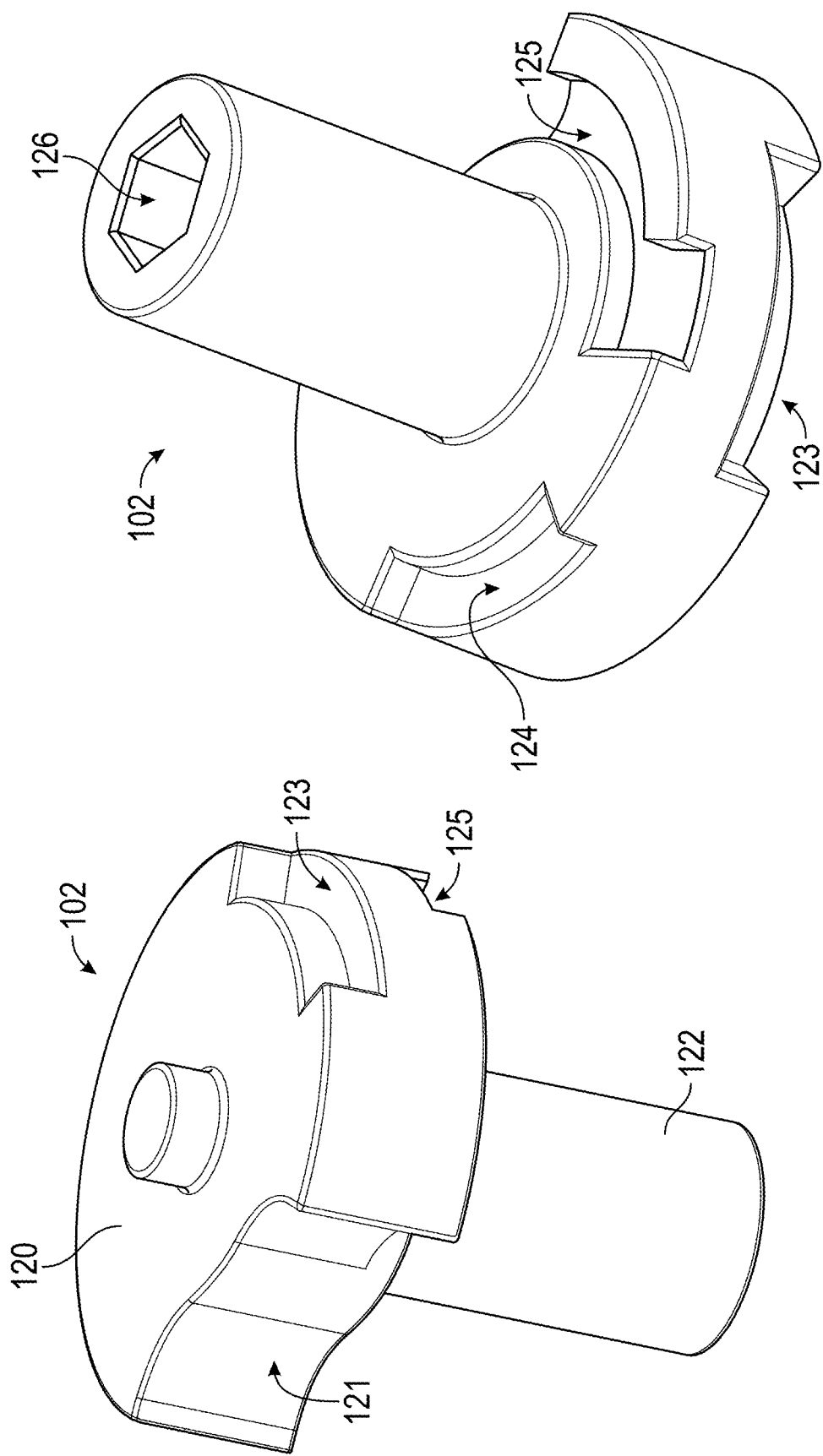
FIG. 2A is a top perspective view of a valve of the fluid sensor module in FIG. 1A.
FIG. 2B is a bottom perspective view of the valve of the fluid sensor module in FIG. 1A.

FIGS. 2A-2B shows a top perspective view and a bottom perspective view of the valve 102, respectively. The valve 120 can comprise a valve head 120 and a valve connector shaft 122. The valve connector shaft 122 can include motor shaft opening 126 such that the valve connector shaft 122 is configured to be positioned in a valve seat 132 of the housing 103 (see FIG. 3A). The valve 120 can further include recesses to enable the fluid sensor module 100 to operate in different positions or modes as discussed below. For example, the valve 120 can comprise a through recess 121, an upper partial recess 123, a first lower partial recess 124, and a second lower partial recess 125.

Figure 3A:
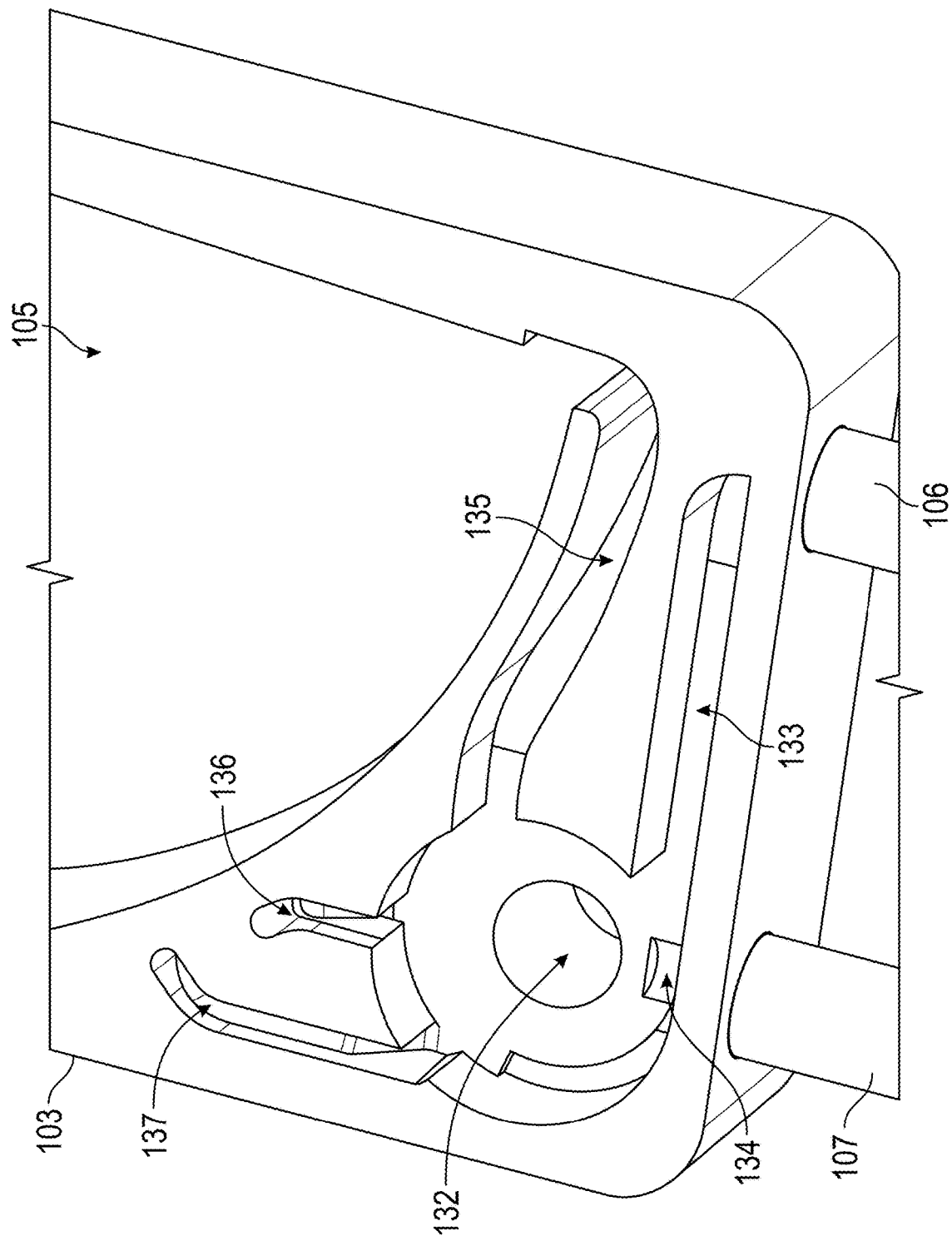
FIG. 3A is a top side perspective view of a housing of the fluid sensor module in FIG. 1A.
Figure 3B:
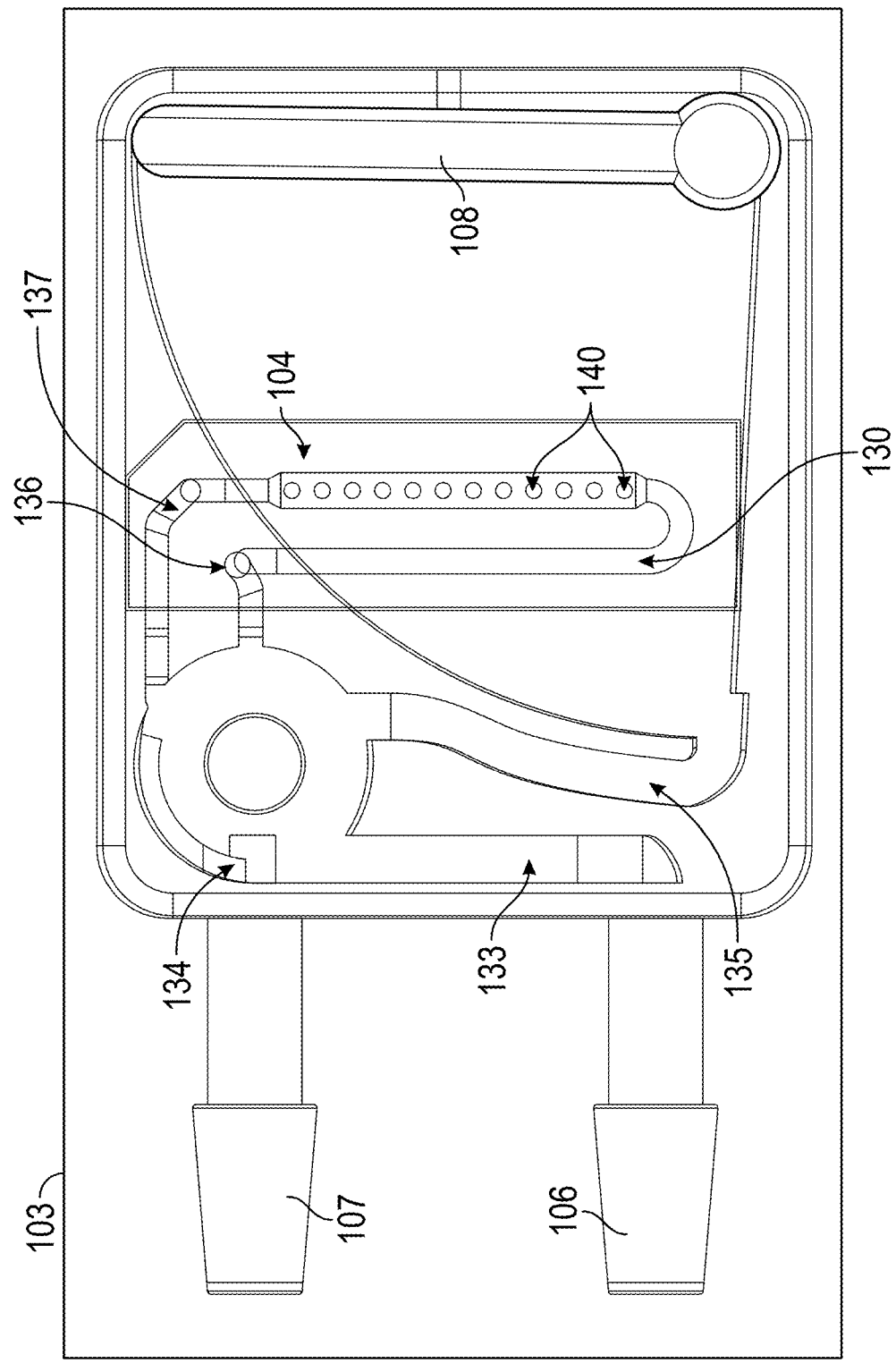
FIG. 3B is a top side sectional view of the housing and a sensing assembly of the fluid sensor module in FIG. 1A.

FIGS. 3A-3B shows additional details of the housing 103. The housing 103 of the fluid sensor module 100 can have an inlet channel 133 fluidly connected to the fluid inlet 106 and an outlet channel 134 fluidly connected to the fluid outlet 107. A fluid can be provided to the valve 120 through the inlet channel 133 and out of the valve 120 through the outlet channel 134. A valve seat 132 can be configured to receive the valve 120. A calibration channel 135 can fluidly connect the valve 120 to the calibration fluid reservoir 105. The housing 103 can hold the plunger 108 in the calibration fluid reservoir 105 as shown in FIG. 3B. A sample fluid can be provided to the sensing assembly 104 by flowing through the fluid pathway 130 configured to expose the sample fluid to the electrodes 140 of the sensing assembly 104. The sample fluid can enter the fluid pathway 130 through a sample entry channel 136 and exit through a sample exit channel 137.

Figure 4A:
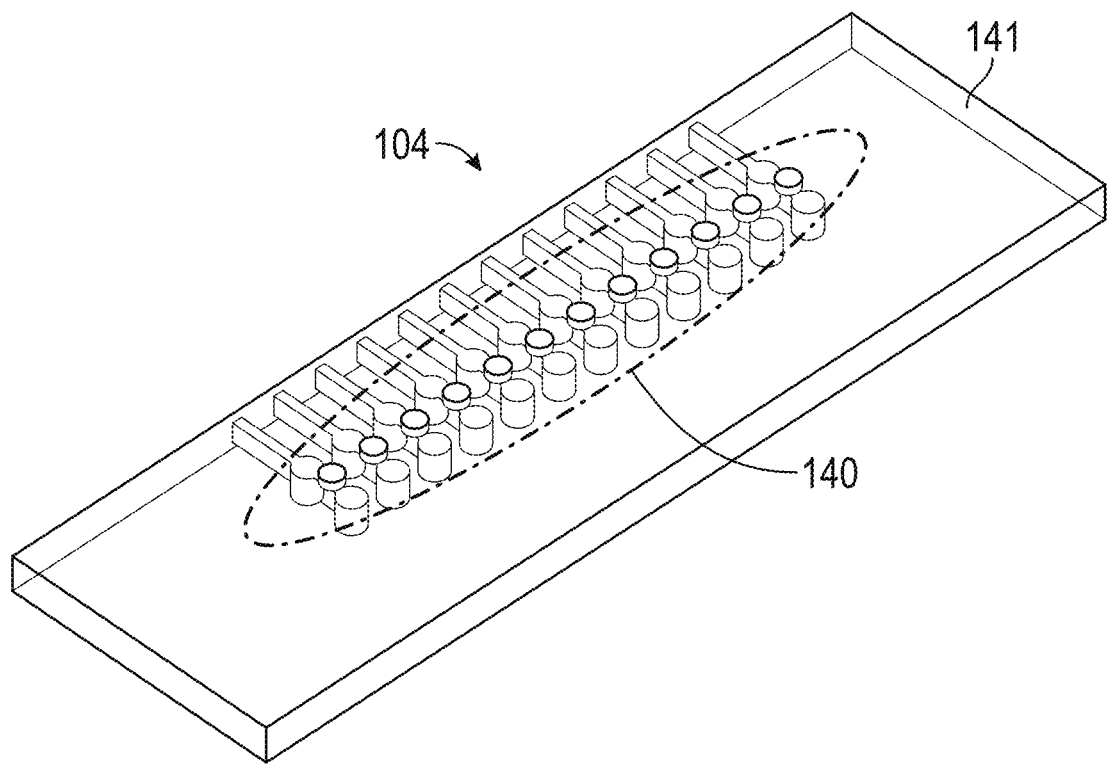
FIG. 4A is a top perspective view of the sensing assembly of the fluid sensor module in FIG. 1A.
Figure 4B:
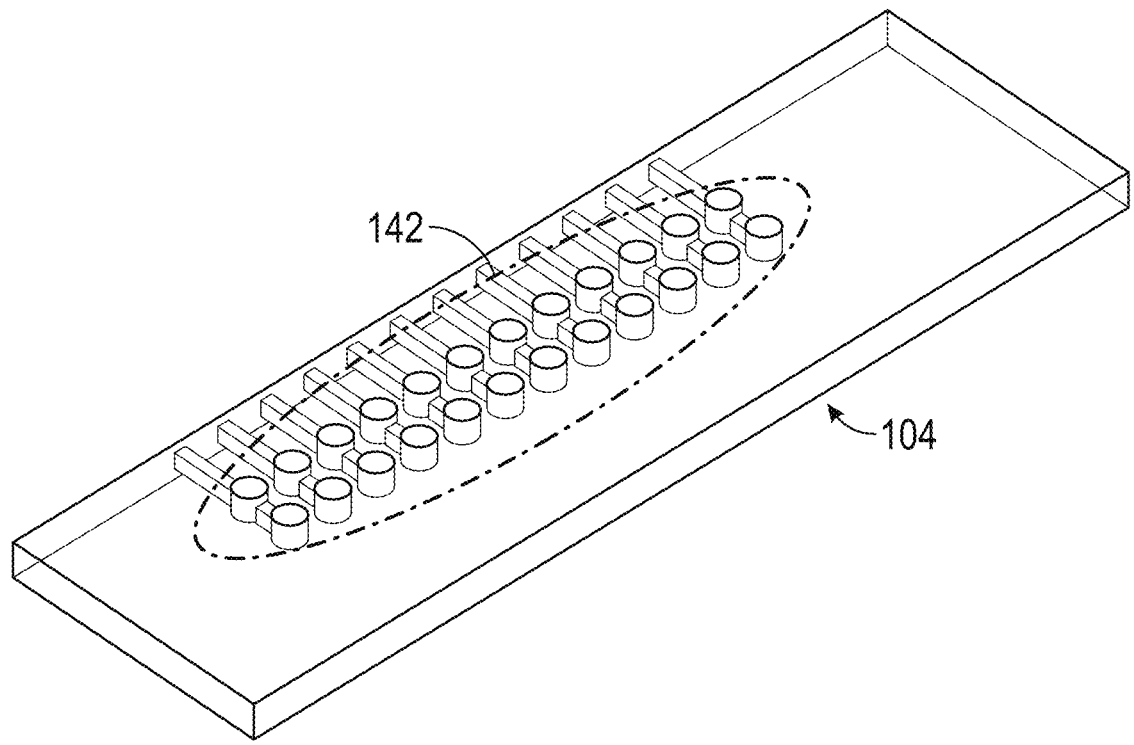
FIG. 4B is a bottom perspective view of the sensing assembly of the fluid sensor module in FIG. 1A.

FIGS. 4A-4B shows additional details of the sensing assembly 104. The sensing assembly 104 can comprise a plastic mold 141 with electrodes 140 embedded in the plastic mold 141 and exposed to the ambient from one side of the plastic mold 141. The sensing assembly 104 can have I/O pads 142 exposed to the ambient from the other side of the plastic mold 141.

Figure 5A:
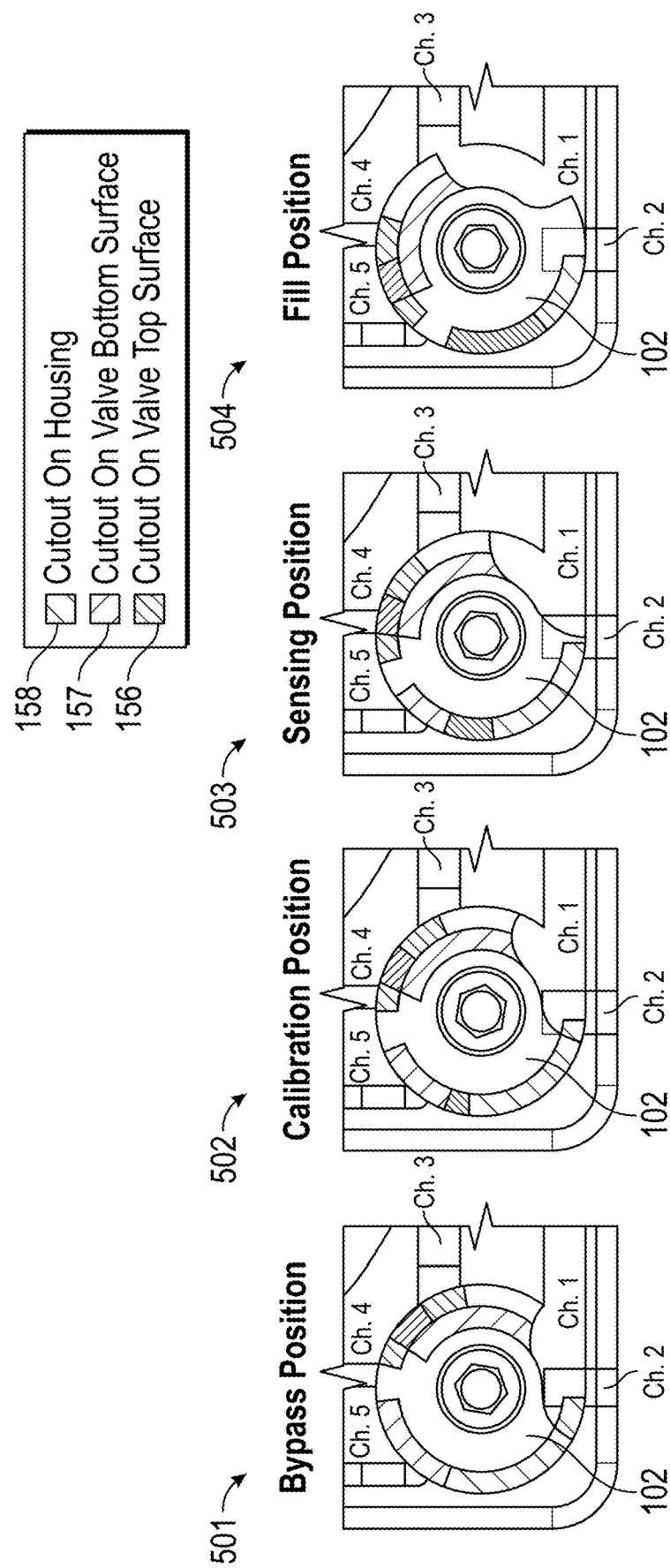
FIG. 5A is an illustration of the valve of the fluid sensor module in FIG. 1A in four different positions.

During a treatment procedure, the fluid sensor module can operate in a plurality of modes. As shown in FIGS. 5A-5K, a valve can have a plurality of positions configured to place the fluid sensor module in the plurality of modes. The plurality of modes can include a bypass position 501, a calibration position 502, a sensing position 503, and a fill position 504. These positions can be enabled by rotating the valve 102 and aligning the cutouts on the valve 102 with different channels or cutouts on the housing 103. On the valve 102, there can be a cutout on valve top surface 156 (e.g. upper partial recess) and two cutouts on valve bottom surface 157 (e.g. first and second lower partial recess) as shown in FIG. 5A. On the housing 103, there can be a cutout on housing 158 and channels 1 through 5 (see FIG. 5A). Channel 1 can correspond to the inlet channel 133; channel 2 can correspond to the outlet channel 134; channel 3 can correspond to the calibration channel 135; channel 4 can correspond to the sample entry channel 136; and channel 5 can correspond to the sample exit channel 137.

For example, in a bypass mode 510, the valve 102 can be placed in the bypass position 501. A valve motor disposed in a reader can connect to the valve 102 of the fluid sensor module 100 by way of a valve connector (e.g., a valve opening) configured to operably connect to a motor shaft of the valve motor. Processing electronics in the reader can be configured to send instructions to the valve motor to place the fluid sensor module in the bypass mode 510 by, e.g., rotating the valve 102 to the bypass position 501. In the bypass position 501, the channels 1 and 2 can be connected to each other allowing a fluid to flow through while the channels 3, 4, 5 are blocked by the valve head 120 (see FIGS. 5A-5C). The through recess 121 of the valve 102 can connect channel 1 (e.g. the inlet channel 133) and channel 2 (e.g., the outlet channel 134) as shown in FIG. 5C. A sample fluid 51 (such as the patient's blood, peritoneal dialysate, etc.) can enter a housing of the module by way of a fluid inlet through the channel 1 and exit the housing through the channel 2 (see FIG. 5B). In the bypass mode 510, the valve can directly connect the fluid inlet to a fluid outlet to convey the sample fluid outside the housing. In the bypass mode 510, therefore, the sample fluid (e.g., the patient's blood, peritoneal dialysate, etc.) may not be monitored by the sensor module, but may instead be recirculated to the treatment system.

Figure 5B:
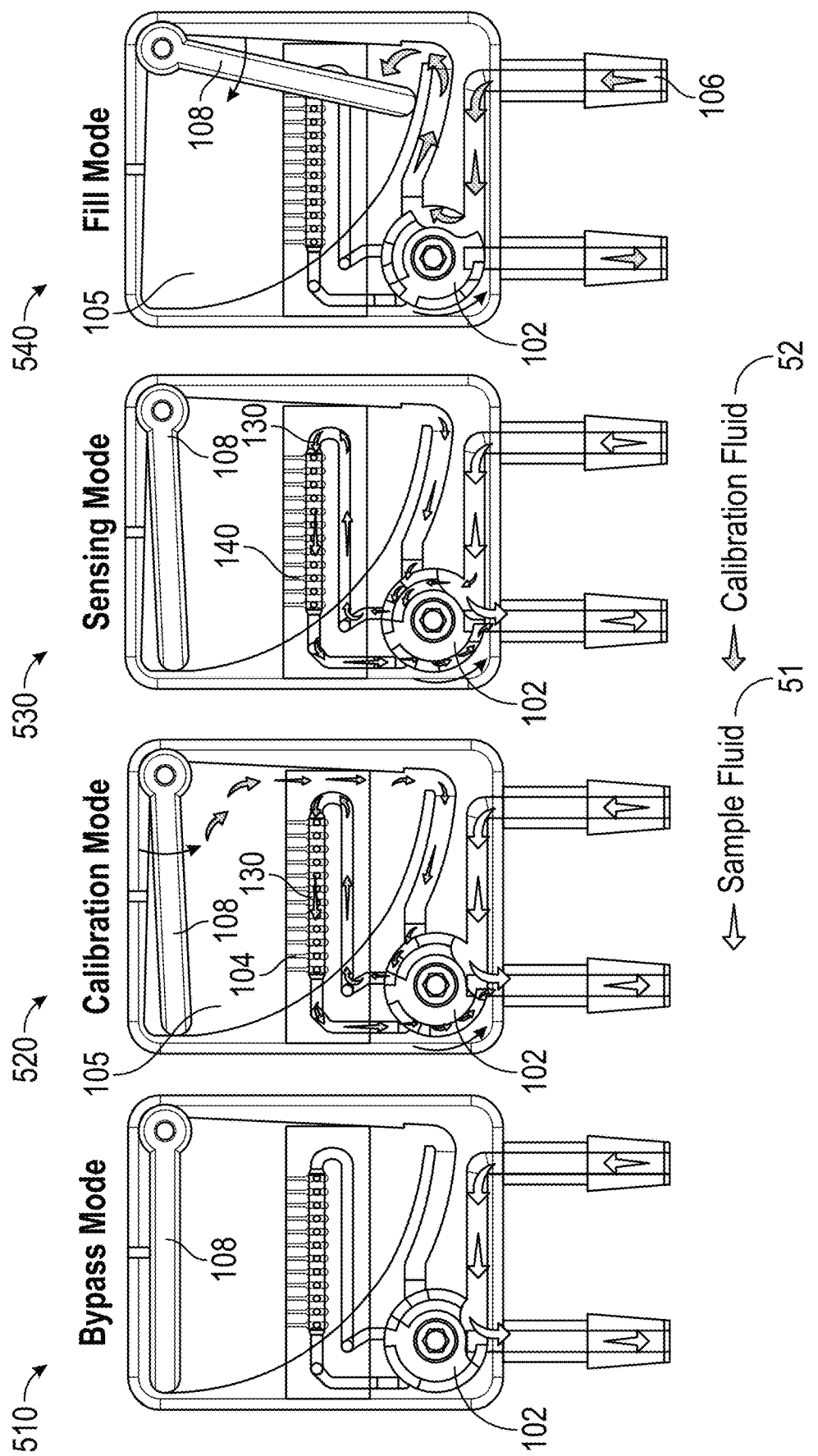
FIG. 5B is an illustration of the fluid sensor module in FIG. 1A and the flows of fluids in the fluid sensor module in the four different positions.
Figure 5C:
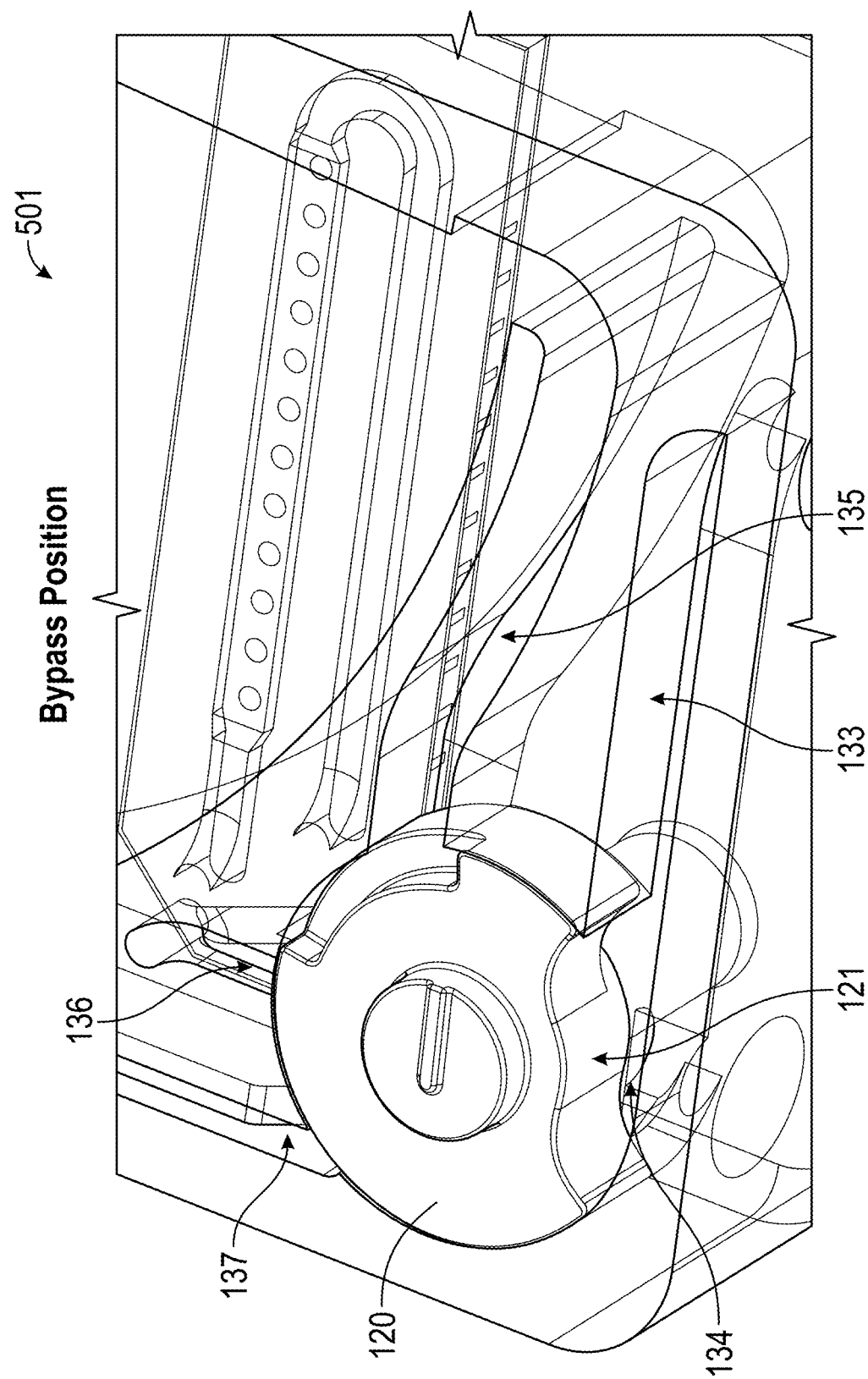
FIG. 5C is a magnified right side perspective view of the fluid sensor module in FIG. 1A in a bypass position.
Figure 5D:
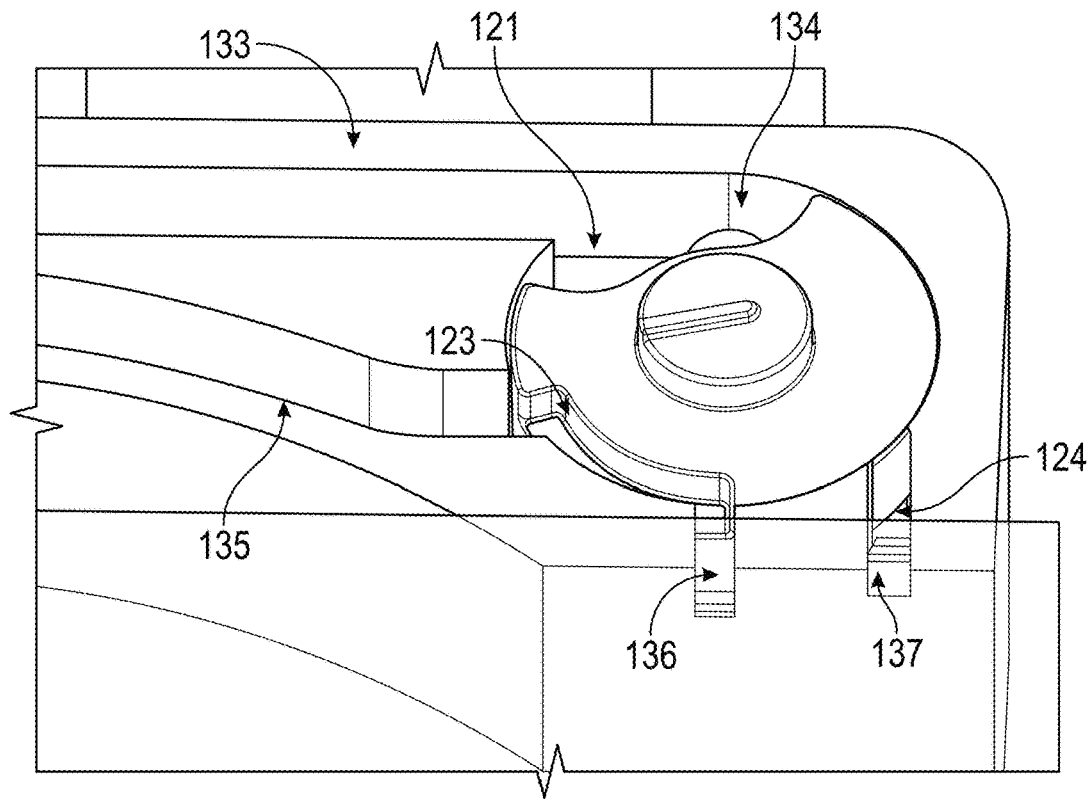
FIG. 5D is a magnified sectional view of the fluid sensor module in FIG. 1A in a calibration position.
Figure 5E:
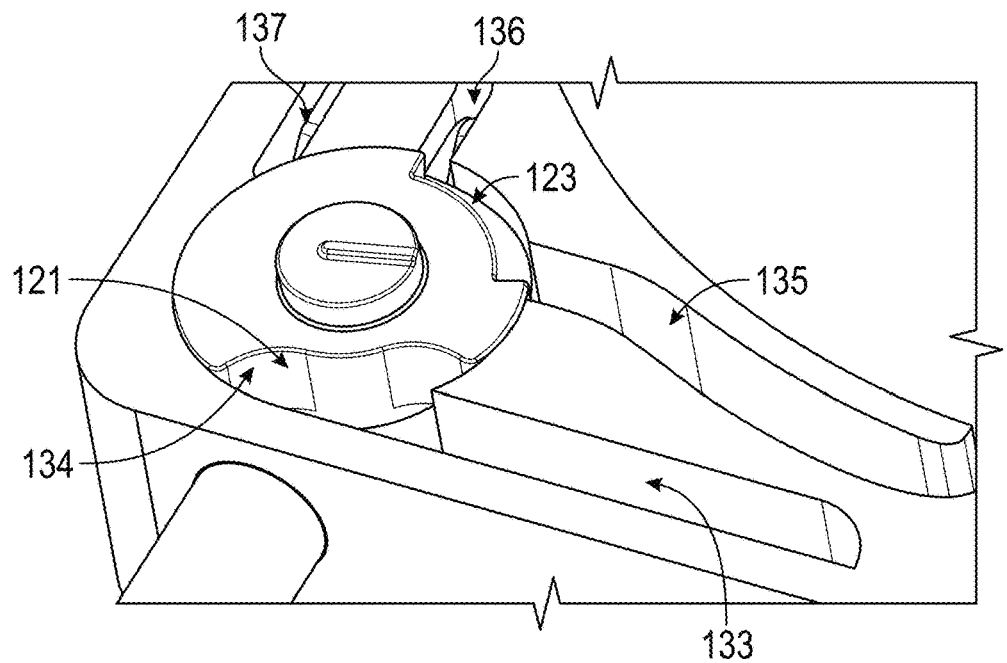
FIG. 5E is a magnified right side perspective view of the fluid sensor module in FIG. 1A in the calibration position.

During a calibration mode 520, the valve motor can place the valve 102 in the calibration position 502 as shown in FIGS. 5A-5B and 5D-5E. As shown in FIG. 5B, calibration fluid 52 (also referred to as a quality control fluid, or QC fluid, e.g., a biocompatible fluid such as water, saline, etc.) can be provided in a calibration reservoir 105 of the housing. In the calibration position 502, as in the bypass position 501, the sample fluid 51 can pass directly from the fluid inlet to the fluid outlet to bypass the sensing assembly. That is, channel 1 (e.g. the inlet channel 133) and channel 2 (e.g. the outlet channel 134) can be connected by the through recess 121 (see FIG. 5D). As shown in FIGS. 5A-5B, the valve 102 can fluidly connect the calibration channel 135 that is connected to the calibration reservoir 105 to the sample entry channel 136 that is in fluid connection with the fluid pathway 130 and the sensing assembly 104. That is, channels 3 and 4 can be connected by the upper partial recess 123 (see FIG. 5D). Finally, in a calibration position 502, in some embodiments, the calibration fluid can exit the fluid pathway 130 and the sensing assembly 104 by way of a sample exit channel 137 and the outlet channel 134. That is, the channel 5 and the channel 2 can be connected by the first lower partial recess 124 (see FIG. 5D). In some embodiments, the calibration fluid can be entrained with the sample fluid and recirculated into the patient's body. In other embodiments, during calibration, the calibration fluid can be redirected to a separate waste container as shown in FIGS. 11 and 12 and discussed further below, which may be disposed of and may not be circulated into the patient's body.

During the calibration mode 520, processing electronics of a reader connected to a fluid sensor module can send instructions to a plunger motor of the reader. The plunger motor can rotate the plunger 108 of the fluid sensor module 100 by a specified amount to drive a predetermined volume of the calibration fluid from the reservoir 105, through the calibration channel 135, and into the fluid pathway 130 to purge the electrodes of the sensing assembly 104 of sample fluid and any other materials as shown in FIG. 5B. The fluid sensor module may be disposable, and the calibration reservoir fluid may be filled in to the reservoir at the factory with a volume sufficient for a preset number of purges, and the plunger rotated about its pivot by the motor through a small angle (e.g., 90°/preset number of purges) for each purge. Thus, in each purge or calibration cycle, the motor can rotate the plunger by a predetermined amount to deliver a predetermined volume of calibration fluid to the sensing assembly. The calibration fluid and the calibration mode can serve to reset the sensor module by flushing the sensing assembly of older sample fluid and/or other debris. Thus, the calibration fluid may also be deemed a purge fluid. The processing electronics can be configured to recognize that the sample fluid is in fluid communication with each of the electrodes.

Figure 5F:
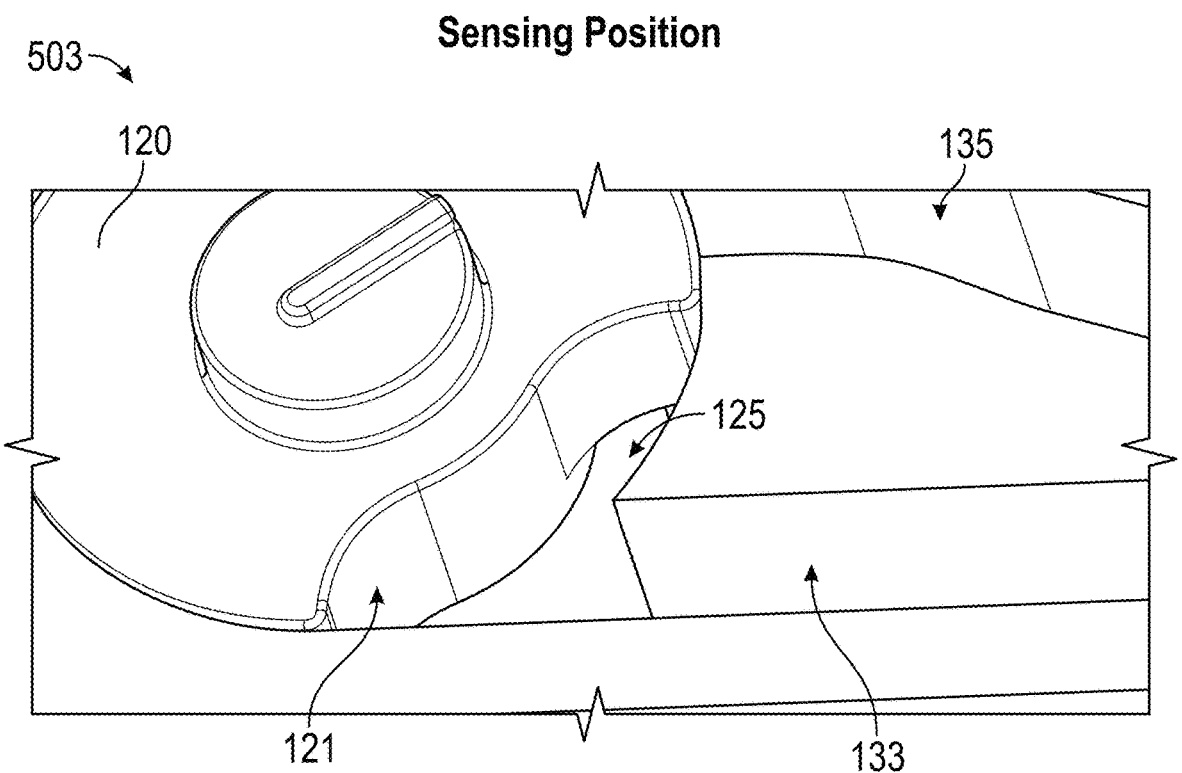
FIG. 5F is a magnified right side perspective view of the fluid sensor module in FIG. 1A in a sensing position.
Figure 5G:
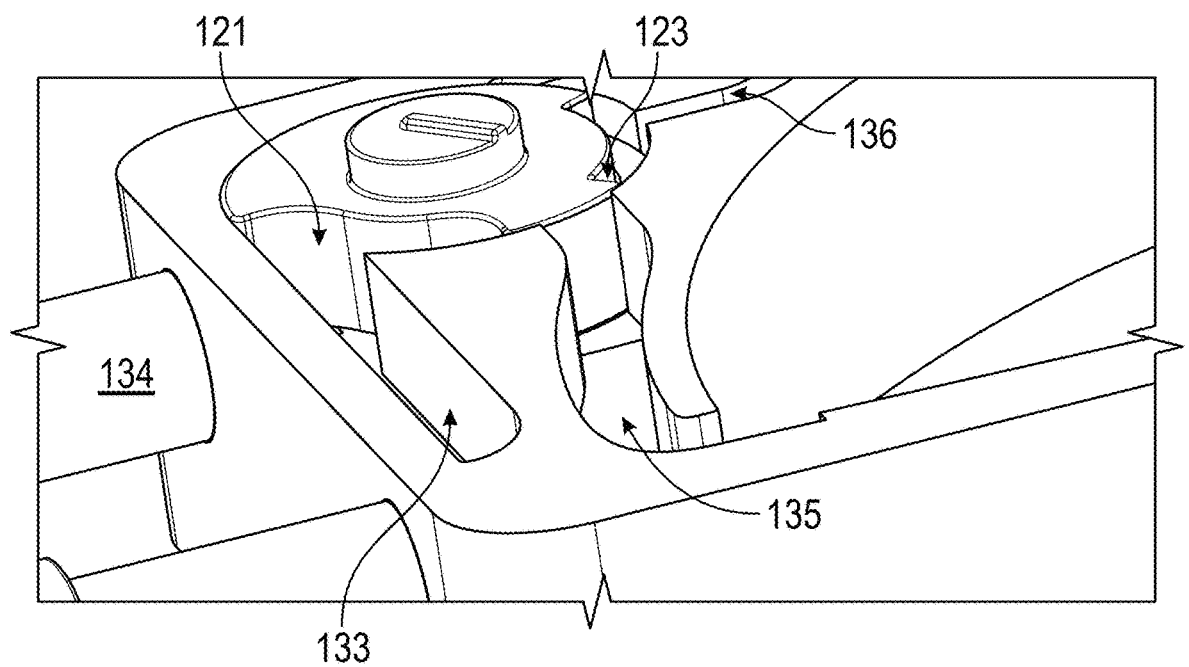
FIG. 5G is a back perspective view of the fluid sensor module in FIG. 1A in the sensing position.
Figure 5H:
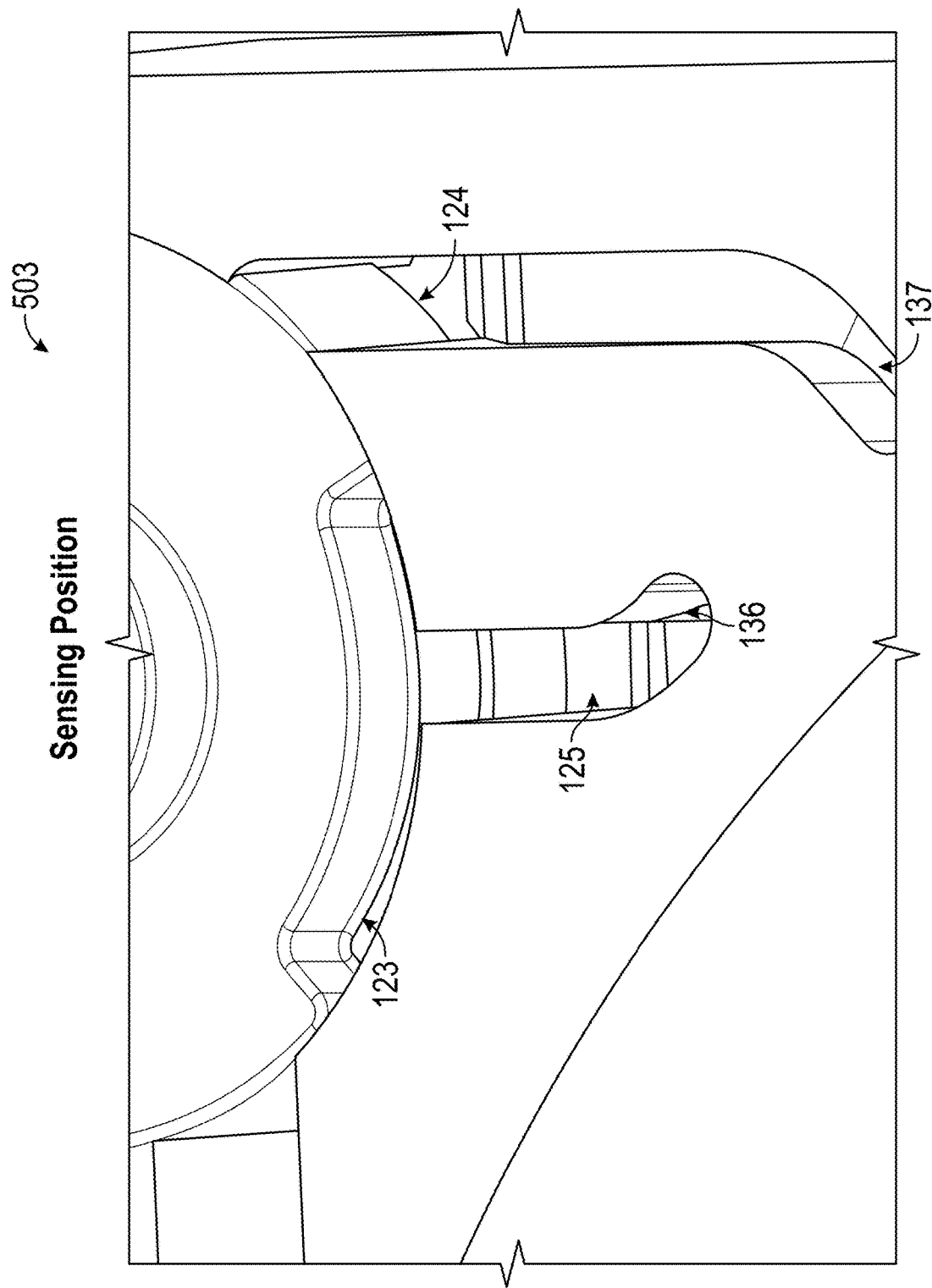
FIG. 5H is a magnified left side perspective view of the fluid sensor module in FIG. 1A in a sensing position.

During a sensing mode 530, the valve motor of the reader can rotate the valve 102 of a fluid sensor module 100 to the sensing position 503 as shown in FIGS. 5A-5B and 5F-5I. In the sensing position 503, the sample fluid 51 can flow through the fluid pathway 130 and interact with the electrodes 140 (see FIG. 5B). As shown in FIGS. 5A and 5F-5G, the channel 3 (e.g. the calibration channel 135) can be blocked by the valve head 120 and the channel 1 (e.g. the inlet channel 133) and the channel 2 (e.g. the outlet channel 134) can be partially connected by the through recess 121 such that only a portion of the sample fluid 51 can exit the module 100 and the other portion of the sample fluid 51 can go to the fluid pathway 130 for sensing. In some embodiments, the through recess can be sized to prevent a bypass of the sample fluid such that substantially all sample fluid is transferred to the fluid pathway. As shown in FIGS. 5A and 5H-5I, the channel 1 (e.g. the inlet channel 133) and the channel 4 (e.g. the sample entry channel 136) can be fluidly connected by the second lower partial recess 125 and the channel 5 (e.g. the sample exit channel 137) and the channel 2 (e.g. the outlet channel 134) can be fluidly connected, allowing the sample fluid 51 to flow into and out of the fluid pathway 130 as shown in FIG. 5B. When the sample fluid 51 interacts with the electrodes 140, in response, the electrodes 140 can transmit a signal to the I/O pads 142 of the sensing assembly 104 and the leads of the reader indicative of respective constituent components of the sample fluid 51. The processing electronics of the reader or the computing device in communication with the reader can determine an amount of each constituent component detected by the sensor module. If the amount exceeds or is below a threshold for that component, the processing electronics can be configured to send an alert to the clinician and/or modify the treatment procedure (e.g., shut off the procedure, change the parameters of the procedure, etc.).

The processing electronics of the reader can be programmed to automatically switch between various modes of the fluid sensor module. For example, the process electronics can be programmed to automatically cycle between the sensing mode (in which the constituent component(s) of the sample fluid are monitored) and the calibration mode (in which the calibration fluid flushes the sensing assembly). In some embodiments, the processing electronics can be further configured to automatically switch into the bypass mode when the sensing device is to be inactive. In some embodiments, the user (e.g., patient or clinician) can manually switch modes by engaging a user interface (UI) of the reader. The UI of the reader can comprise a touch screen and/or buttons that enable the user and/or clinician to interact with the reader. In some embodiments, the UI can include a display that indicates the levels of the constituent fluids.

Figure 5J:
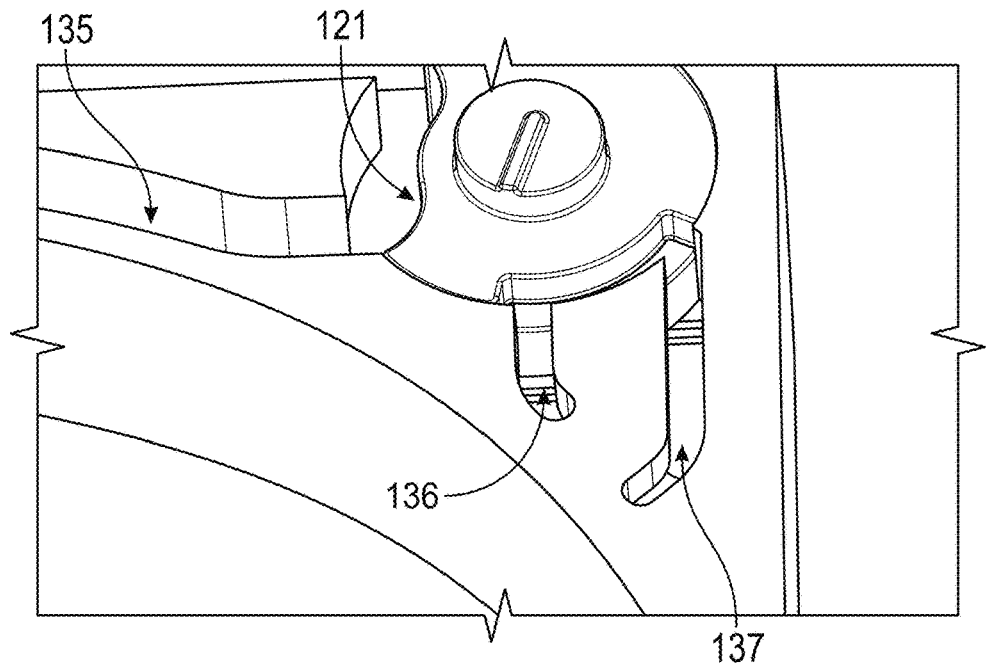
FIG. 5J is a magnified left side perspective view of the fluid sensor module in FIG. 1A in a fill position.
Figure 5K:
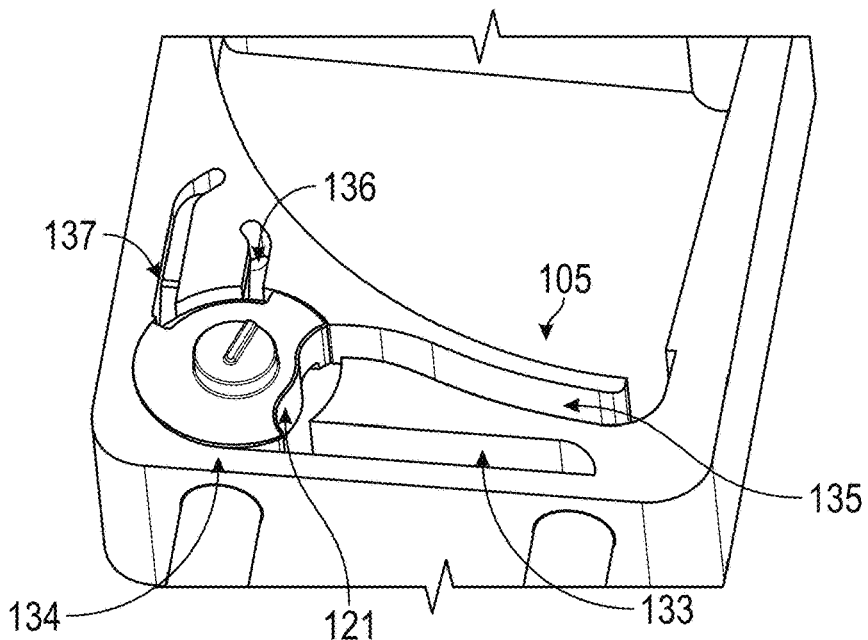
FIG. 5K is a magnified right side perspective view of the fluid sensor module in FIG. 1A in a fill position.

In addition, the sensor module can include a fill mode 540 by rotating the valve 102 to a fill position 504 (see FIGS. 5J and 5K). In the fill mode 540, the calibration fluid 52 can be pumped or otherwise driven into the fluid inlet 106. In some embodiments, as shown in FIG. 5B, the plunger 108 can be rotated/moved (e.g. manually or by the motor of the reader) to drive the calibration fluid 52 to transfer from the fluid inlet 106 to the calibration reservoir 105 by way of the calibration channel 135. Thus, in the fill mode 540, the calibration fluid 52 can travel in a reverse direction along the calibration channel 135 as compared to during the calibration mode 520. As shown in FIG. 5A, channel 1 (e.g. inlet channel 133) and channel 3 (e.g. calibration channel 135) can be fluidly connected by the through recess 121 and channel 2, channel 4, and channel 5 can be blocked. In various embodiments, the calibration reservoir can be filled prior to use, e.g., in the factory or assembly plant.

Figure 6A:
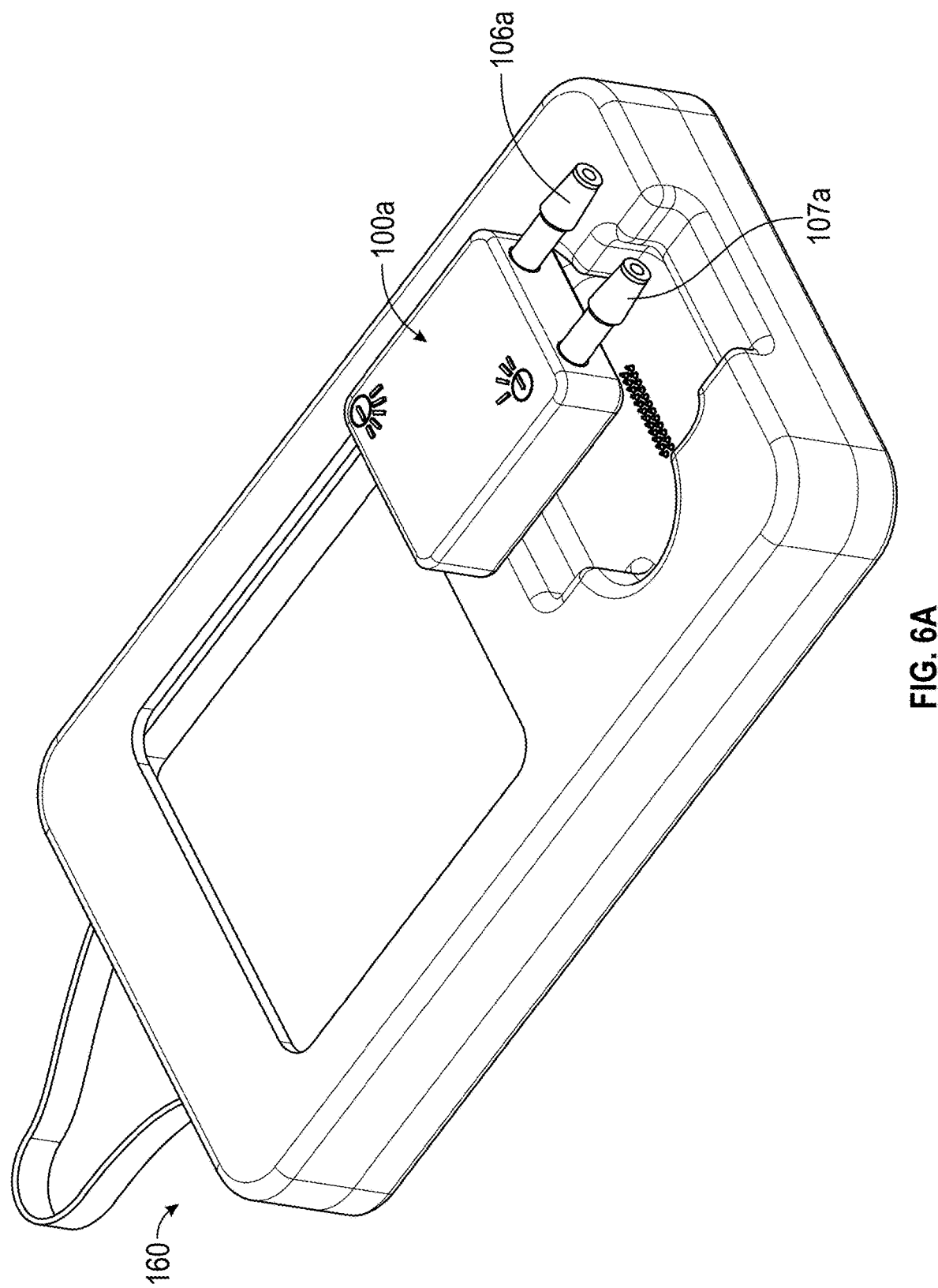
FIG. 6A is a top perspective exploded view of another embodiment of a fluid sensor module in an assembly with a reader.
Figure 6B:
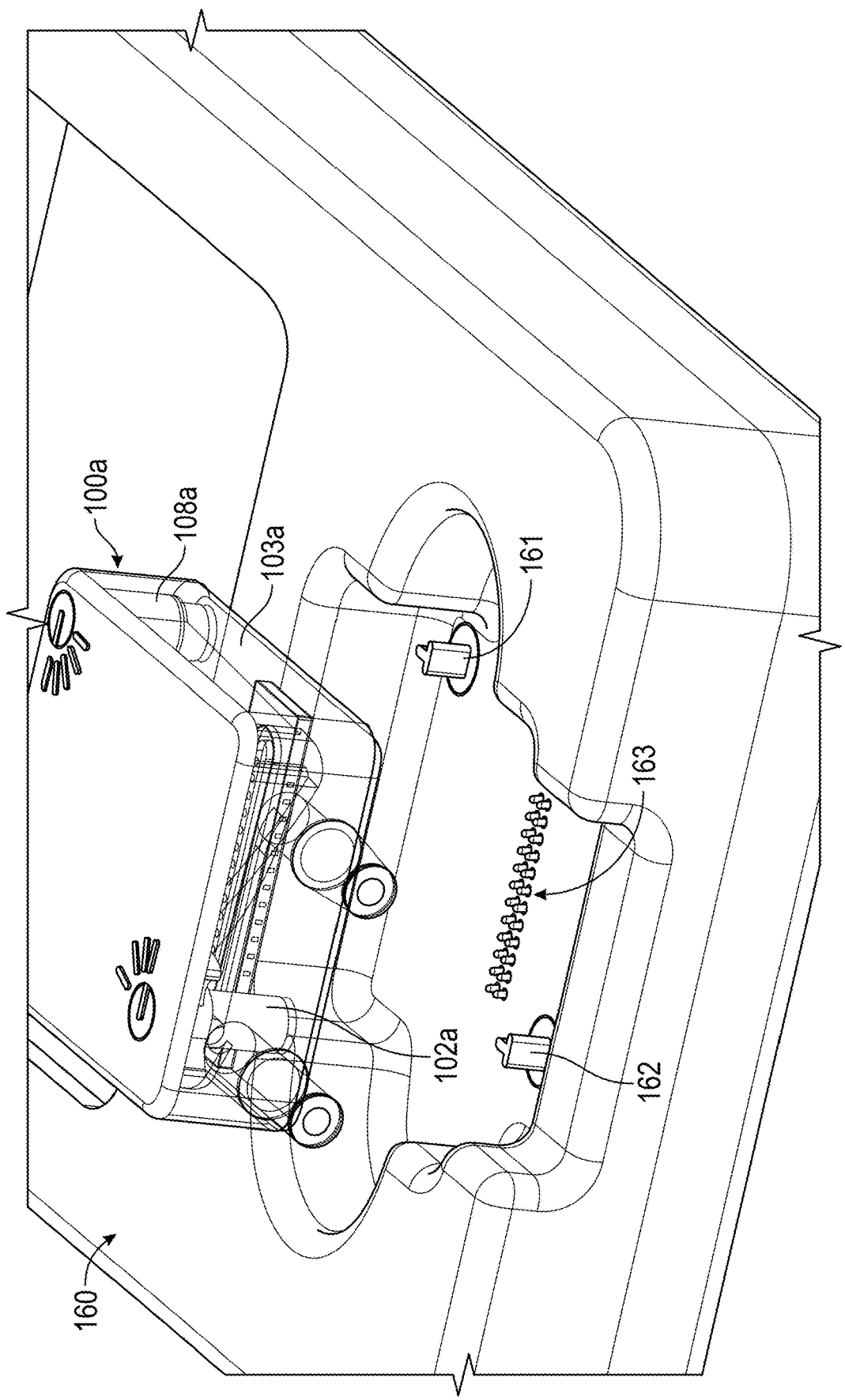
FIG. 6B is a magnified right side perspective exploded view of the fluid sensor module and reader assembly in FIG. 6A.
Figure 6C:
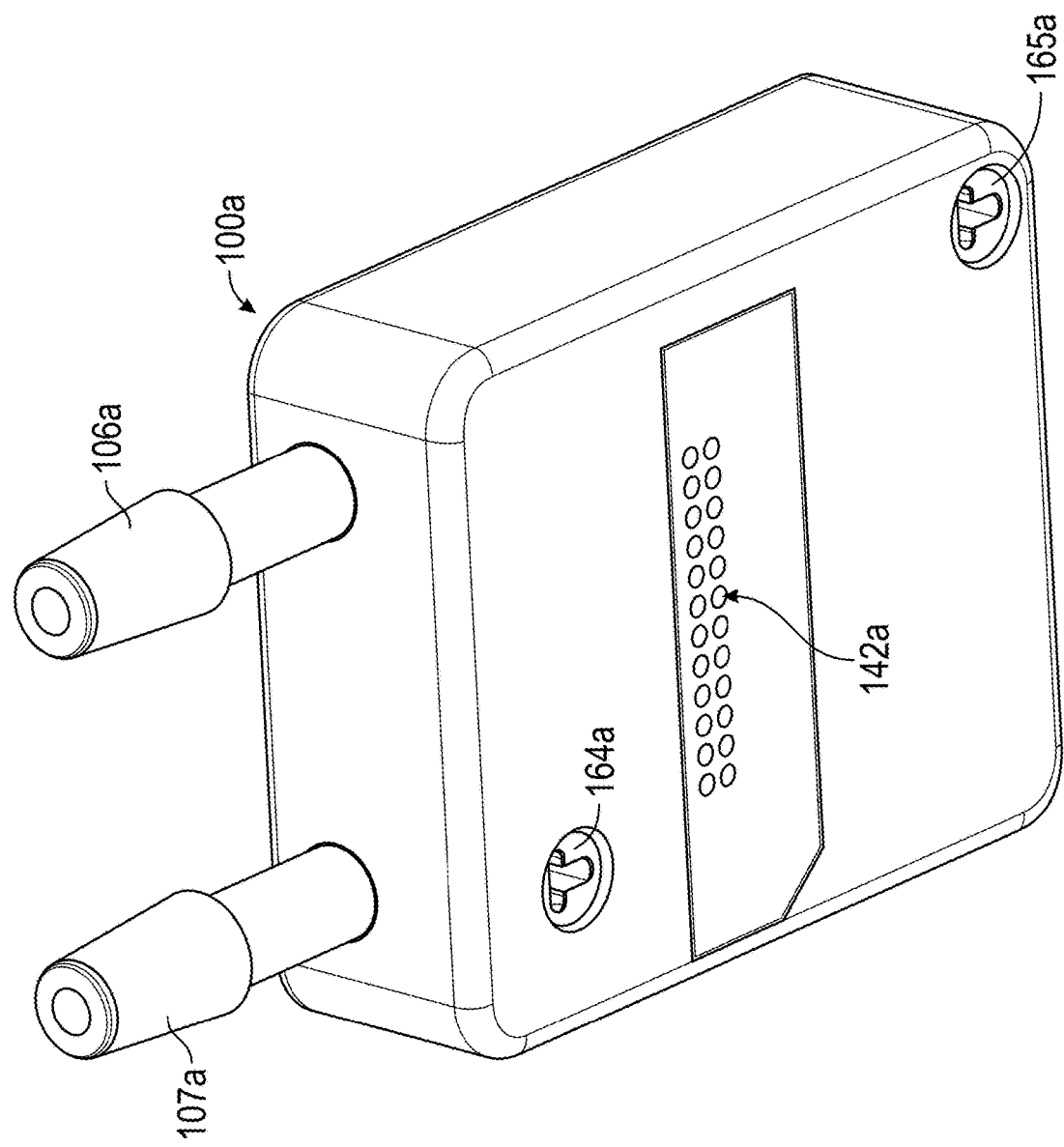
FIG. 6C is a bottom perspective view of the fluid sensor module assembly in FIG. 6A.
Figure 7A:
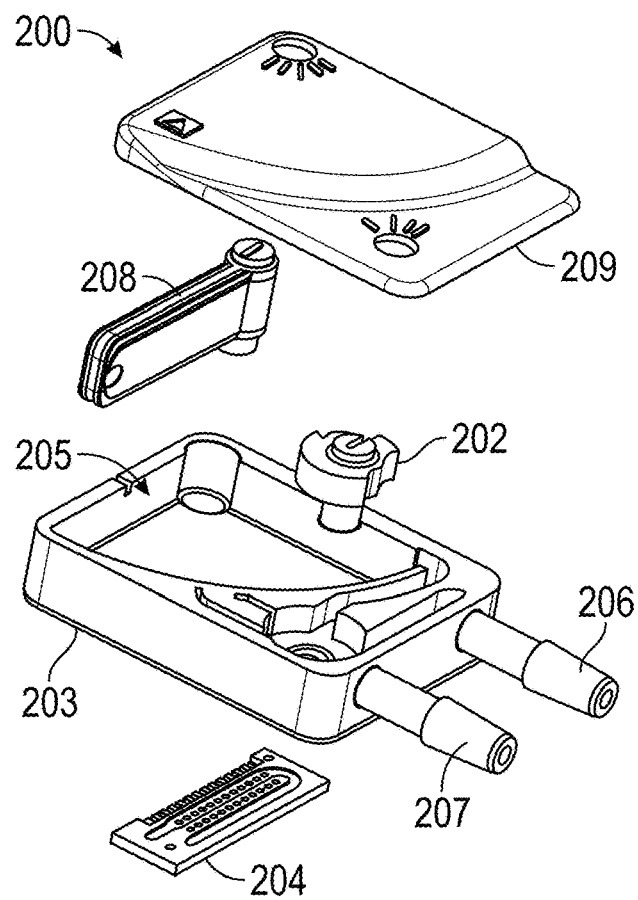
FIG. 7A is a top perspective exploded view of another embodiment of a fluid sensor module.
Figure 7B:
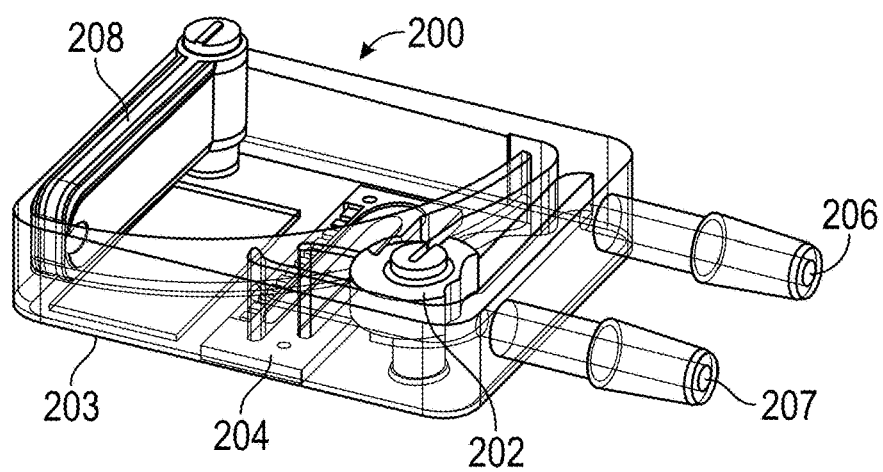
FIG. 7B is an internal view of the fluid sensor module in FIG. 7A.
Figure 8B:
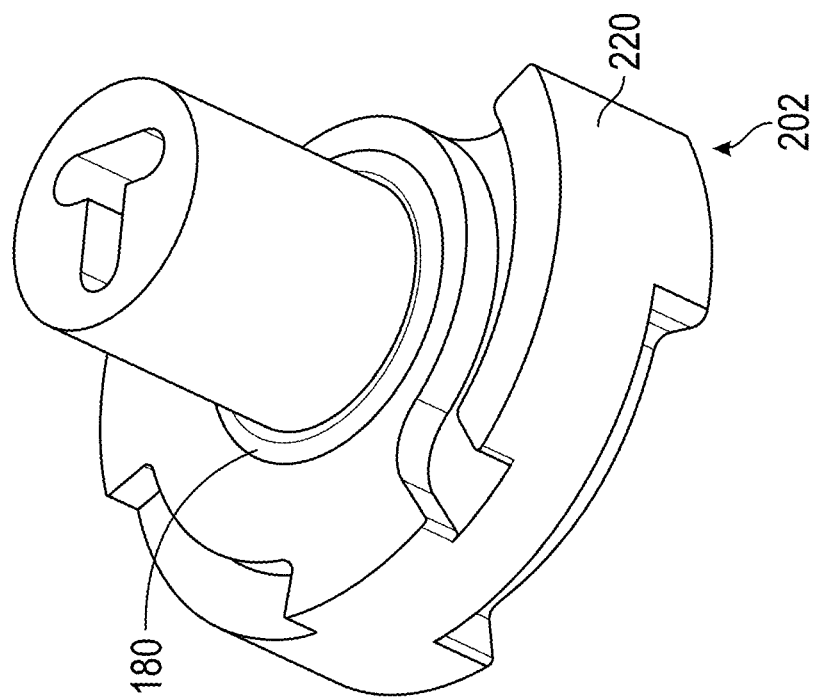
FIG. 8B is a bottom perspective view of a valve of the fluid sensor module in FIG. 7A.
Figure 8A:
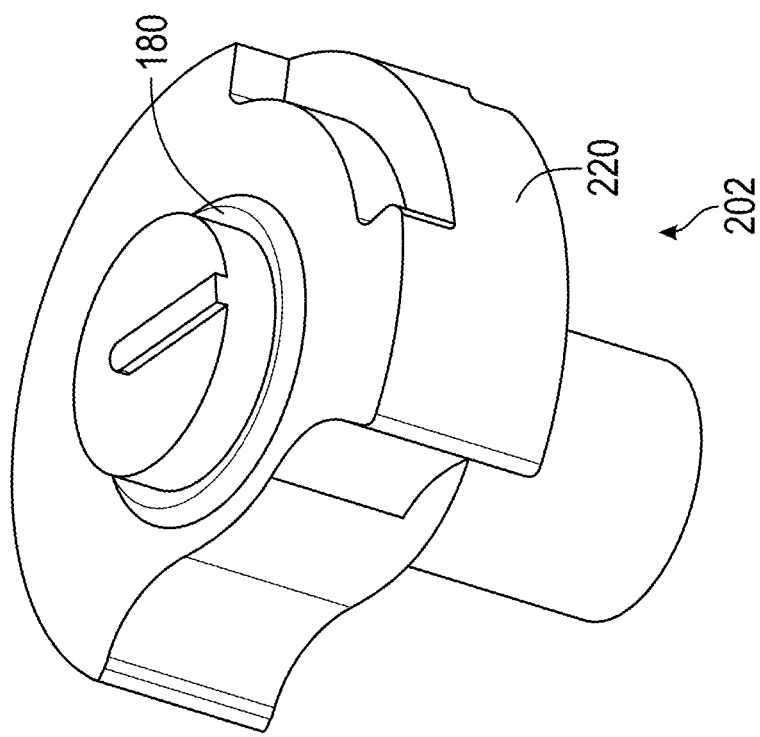
FIG. 8A is a top perspective view of a valve of the fluid sensor module in FIG. 7A.
Figure 9A:
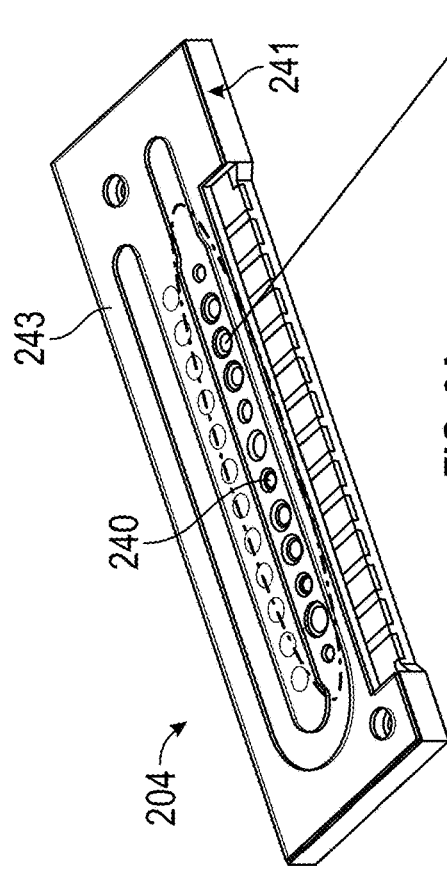
FIG. 9A is a top perspective view of a sensing assembly of the fluid sensor module in FIG. 7A.
Figure 9B:
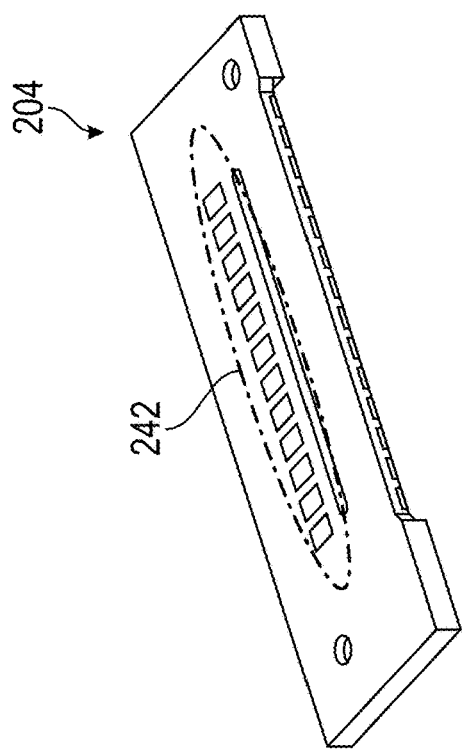
FIG. 9B is a bottom perspective view of the sensing assembly of the fluid sensor module in FIG. 7A.
Figure 9C:
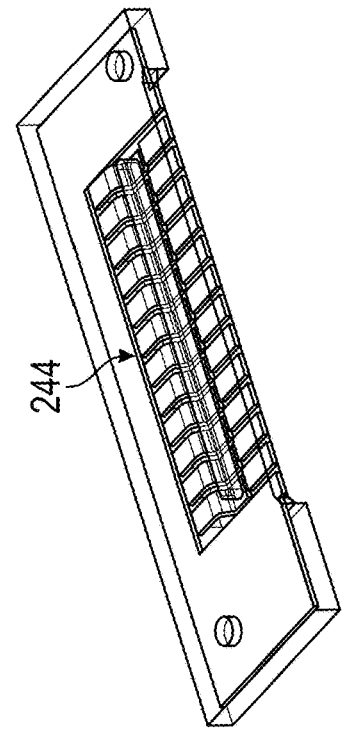
FIG. 9C is an internal view of the sensing assembly of the fluid sensor module in FIG. 7A.
Figure 9D:
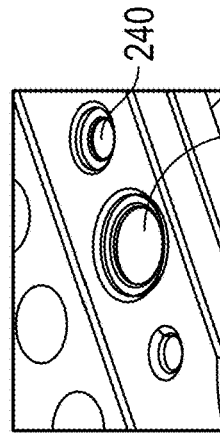
FIG. 9D is a magnified perspective view of the sensing assembly of the fluid sensor module in FIG. 7A.
Figure 9E:
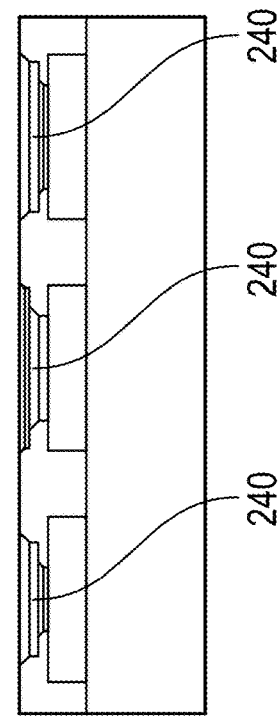
FIG. 9E is a magnified side view of the sensing assembly of the fluid sensor module in FIG. 7A.

FIGS. 6A-6C shows another embodiment of a fluid sensor module in an assembly with a reader. The assembly can include a reader 160, a fluid sensor module 100a comprising a fluid inlet 106a and a fluid outlet 107a. The reader 160 can comprise a plunger motor (not shown) connectable to a plunger 108a in the housing 103a through a first motor shaft 161 on the reader 160 and a corresponding plunger motor connector 165a on the sensor module 100a. The reader 160 can further comprise a valve motor (not shown) connectable to a valve 102a in the housing 103a of the sensor module 100a through a second motor shaft 162 on the reader 160 and a corresponding plunger motor connector 164a on the sensor module 100a. Leads 163 of the reader 160 can electrically connect to corresponding I/O pads 142a of the sensor module 100a. In some embodiments, the reader can comprise processing electronics configured to control the operation of the valve motor and the plunger motor. The processing electronics can also be configured to store and/or process signals transduced by the sensor module and transferred to the leads by way of the I/O pads. In various embodiments, the processing electronics can be configured to identify a constituent composition of the sample fluid. The reader can communicate with a computing device, such as a central server, a mobile device (e.g., a smartphone), a laptop computer, or the like to convey the sensed data to the clinician. For example, the reader can wirelessly transmit the data to the computing device. In other embodiments, the reader can be electrically connected to the computing device by an electrical connector, such as a cable or cord.

Figure 10B:
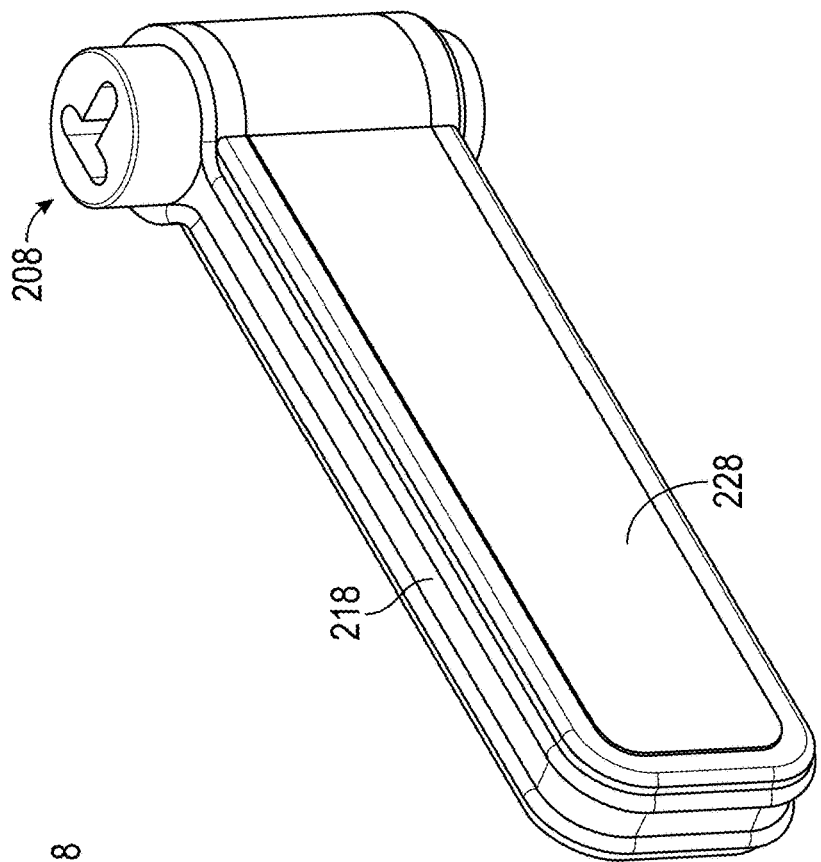
FIG. 10B is a bottom perspective view of the plunger of the fluid sensor module in FIG. 7A.
Figure 10A:
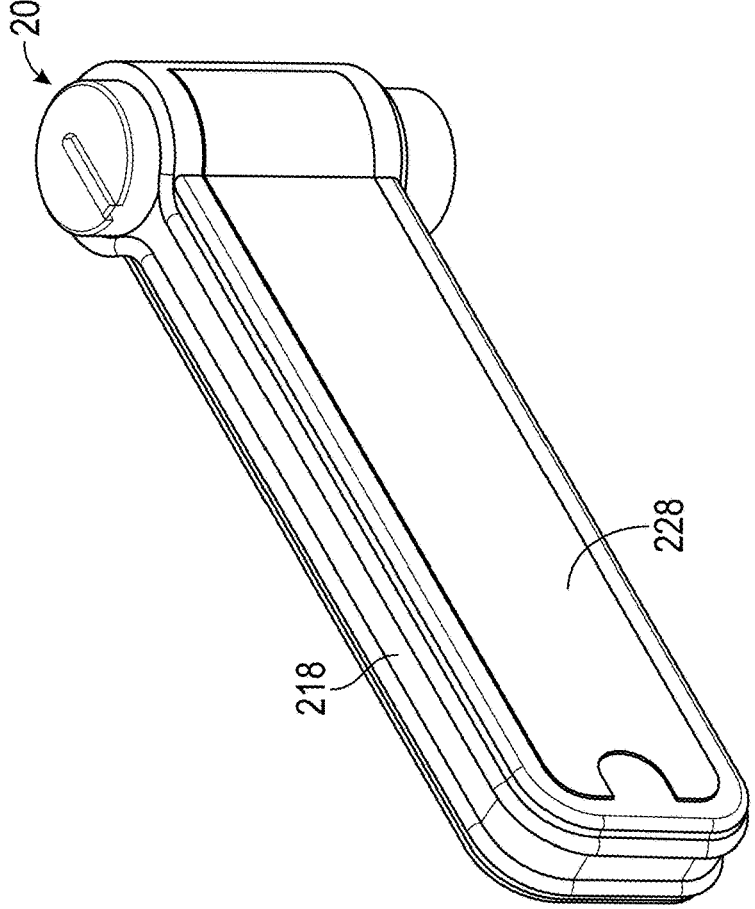
FIG. 10A is a top perspective view of a plunger of the fluid sensor module in FIG. 7A.

FIGS. 7-10 shows another embodiment of a fluid sensor module 200. As shown in FIGS. 7A and 7B, the fluid sensor module 200 can have a housing 203 and a lid 209 enclosing a valve 202, a plunger 208, and a calibration fluid reservoir 205. A sensing assembly 204 can be embedded in the housing 203. The housing 203 can have a fluid inlet 206 and a fluid outlet 207. As shown in FIGS. 8A-8B, the valve 202 can have seals 180 (e.g. O-rings) positioned above and below the valve head 220. As shown in-FIG. 9 FIGS. 9A-9E, the sensing assembly 204 can include pre-formed lead frame 244 configured inside a plastic mold 241. Electrodes 240 can be positioned on top of the sensing assembly 204 and I/O pads 242 can be positioned on bottom of the sensing assembly 204. Adhesive 243 can be applied to the plastic mold 241 to fix the sensing assembly 204 to the housing 203. FIG. 10 shows-FIGS. 10A and 10B show the plunger 208 that can comprise a body 228 and an outer layer 218 wrapped around sides of the body 228.

Figure 11B:
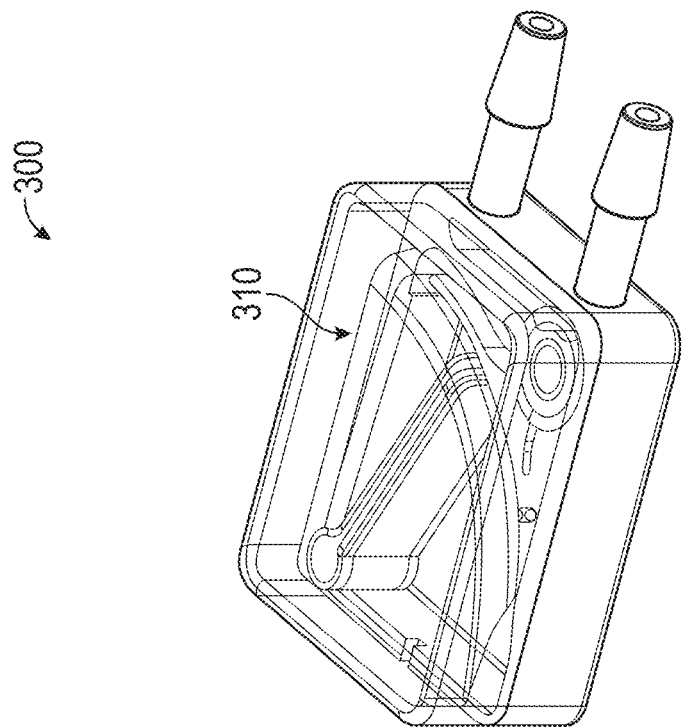
FIG. 11B is an internal view of the fluid sensor module in FIG. 11A.
Figure 11A:
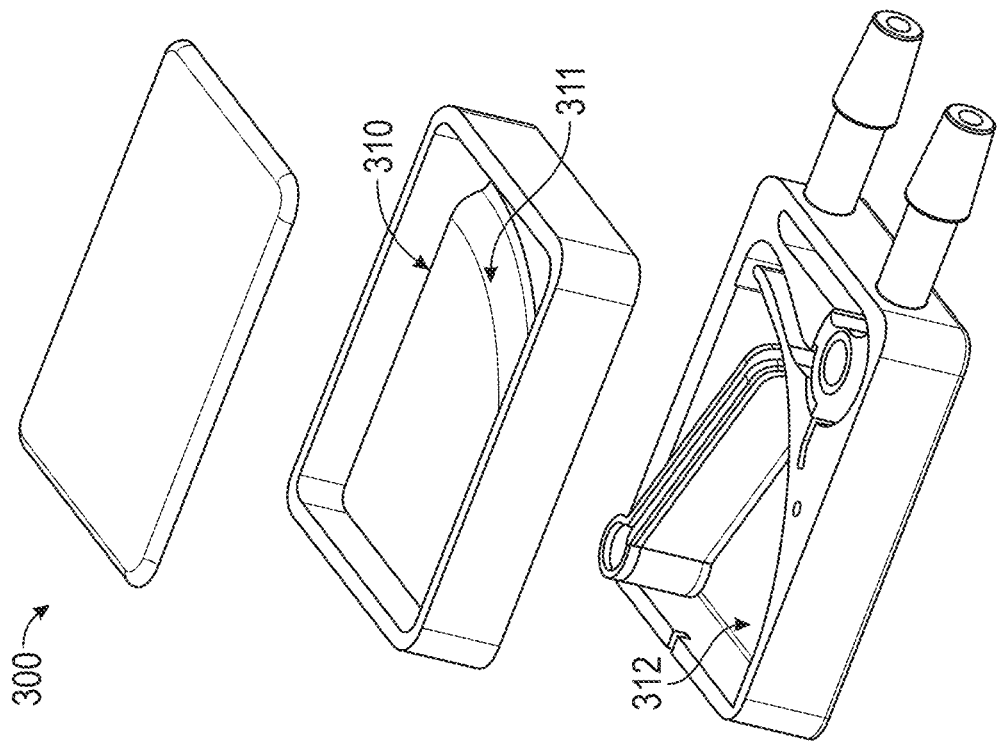
FIG. 11A is an exploded top perspective view of another embodiment of a fluid sensor module.
Figure 12B:
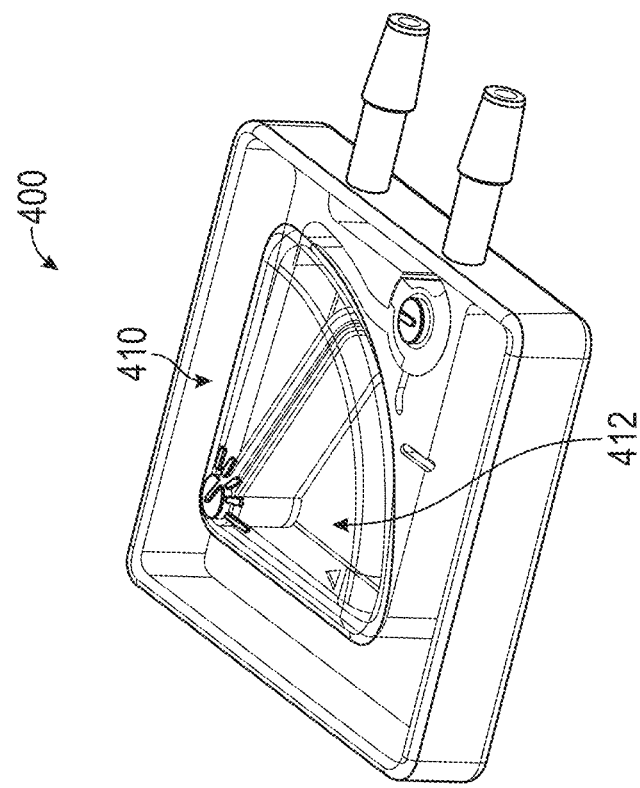
FIG. 12B is an internal view of the fluid sensor module of FIG. 12A.
Figure 12A:
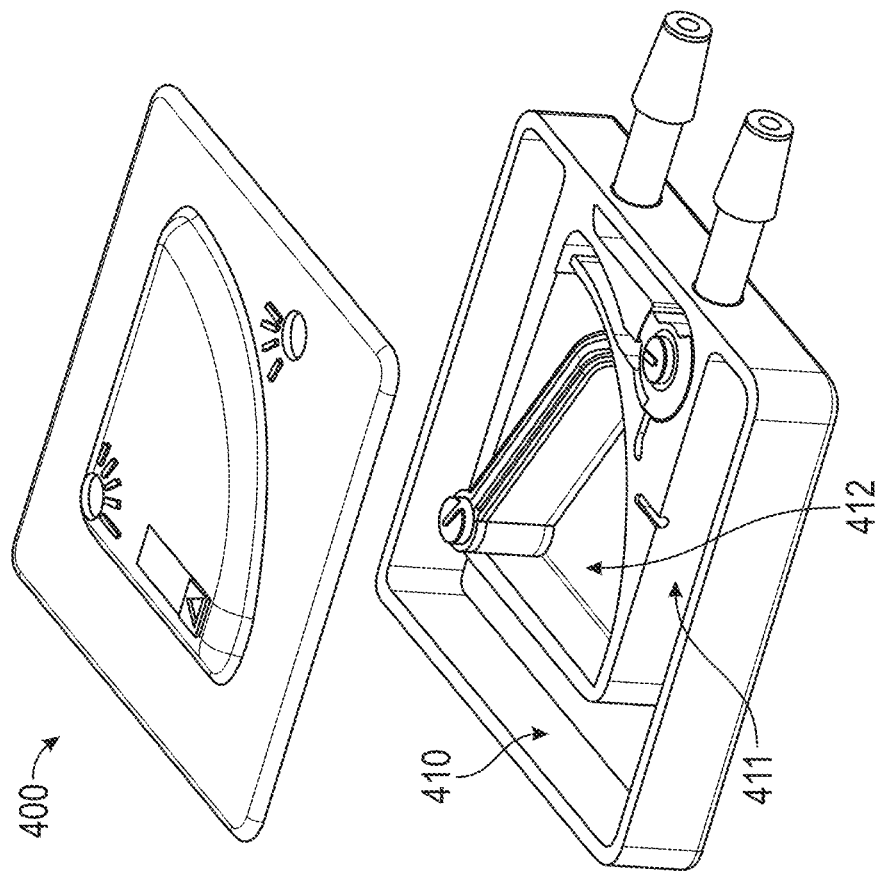
FIG. 12A is an exploded top perspective view of another embodiment of a fluid sensor module.

FIGS. 11A, 11B, 12A, and 12B show additional embodiments of the fluid sensor module. In some embodiments, a waste container 310 can be positioned above a calibration reservoir 312 for a fluid sensor module 300 as shown in FIGS. 11A and 11B. Instead of transferring the used calibration fluid through the outlet and into the medical treatment system and/or patient, the used calibration fluid can alternatively be routed upwardly by way of an internal channel (not shown) to the waste container 310. A partition 311 can separate the used calibration fluid in the waste container 310 from the fresh calibration fluid in the calibration fluid reservoir 312. In FIGS. 11A and 11B, the positioning of the waste container above the calibration fluid reservoir can utilize vertical space above the reservoir to preserve lateral footprint. In some embodiments, a fluid sensor module 400 can include a waste container 410 positioned laterally adjacent a calibration reservoir 412, as shown in FIGS. 12A and 12B. Instead of transferring the used calibration fluid through the outlet and into the medical treatment system and/or patient, the used calibration fluid can alternatively be routed laterally by way of an internal channel (not shown) to the waste container 410. A partition 411 can separate the used calibration fluid in the waste container 410 from the fresh calibration fluid in the calibration fluid reservoir 412. In FIGS. 12A and 12B, the positioning of the waste container 410 laterally adjacent the calibration fluid reservoir 412 can utilize lateral space to vertical height. Additional designs for a waste container may be suitable so as to provide a desired lateral footprint and/or vertical height.

Beneficially, the fluid system disclosed herein can enable the patient to conduct medical treatments (such as dialysis) at home, or otherwise outside of a clinical setting. As one example, when the patient goes to bed for the night, the patient can initiate the dialysis system, and connect the fluid sensor module to the reader. The fluid inlet and fluid outlet of the fluid sensor module can fluidly connect to the treatment system of the medical device, for example, by way of a luer lock or other fluid coupler. The dialysis (or other) machine can be activated, and the sensor module can automatically cycle between bypass mode, calibration mode, and sensing mode (in any suitable order). If an anomaly is detected during the sensing mode, the reader can transmit an alarm to the clinician and/or otherwise modify the treatment procedure automatically. Once the treatment procedure is completed, the patient can disengage the treatment system, and remove the fluid sensor module. The fluid sensor module can be disposed and, for the next treatment procedure, a new fluid sensor module can be inserted into the reader and connected to the medical device.

Although the devices and methods were described to be used with medical treatment and in medical settings, it is to be appreciated that the procedures and devices disclosed herein may be performed on or applied to any kinds of sample or fluid to be tested or sensed with sensors.

Unless the context clearly requires otherwise, throughout the description and the claims, the words "comprise," "comprising," "include," "including" and the like are to be construed in an inclusive sense, as opposed to an exclusive or exhaustive sense; that is to say, in the sense of "including, but not limited to." The word "coupled", as generally used herein, refers to two or more elements that may be either directly connected, or connected by way of one or more intermediate elements. Likewise, the word "connected", as generally used herein, refers to two or more elements that may be either directly connected, or connected by way of one or more intermediate elements. Additionally, the words "herein," "above," "below," and words of similar import, when used in this application, shall refer to this application as a whole and not to any particular portions of this application. Moreover, as used herein, when a first element is described as being "on" or "over" a second element, the first element may be directly on or over the second element, such that the first and second elements directly contact, or the first element may be indirectly on or over the second element such that one or more elements intervene between the first and second elements. Where the context permits, words in the above Detailed Description using the singular or plural number may also include the plural or singular number respectively. The word "or" in reference to a list of two or more items, that word covers all of the following interpretations of the word: any of the items in the list, all of the items in the list, and any combination of the items in the list.

Moreover, conditional language used herein, such as, among others, "can," "could," "might," "may," "e.g.," "for example," "such as" and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments.

While certain embodiments have been described, these embodiments have been presented by way of example only, and are not intended to limit the scope of the disclosure. Indeed, the novel apparatus, methods, and systems described herein may be embodied in a variety of other forms; furthermore, various omissions, substitutions and changes in the form of the methods and systems described herein may be made without departing from the spirit of the disclosure. For example, while blocks are presented in a given arrangement, alternative embodiments may perform similar functionalities with different components and/or circuit topologies, and some blocks may be deleted, moved, added, subdivided, combined, and/or modified. Each of these blocks may be implemented in a variety of different ways. Any suitable combination of the elements and acts of the various embodiments described above can be combined to provide further embodiments. The accompanying claims and their equivalents are intended to cover such forms or modifications as would fall within the scope and spirit of the disclosure.

What is claimed is:

1. A fluid sensor module comprising:
   a sensing assembly;
   a housing;
   a fluid pathway configured to transfer a sample fluid to be in fluid communication with the sensing assembly;
   a valve movable between a sensing position in which the sample fluid is transferred along the fluid pathway and a calibration position in which a calibration fluid is transferred from a calibration fluid reservoir along the fluid pathway;
   a fluid inlet to transfer the sample fluid into the housing; and
   a fluid outlet to transfer the sample fluid out of the housing;
   wherein the valve has a bypass position in which the fluid inlet is directly connected to the fluid outlet such that the sample fluid is conveyed from the fluid inlet to the fluid outlet so as to bypass the fluid pathway, the valve in the bypass position blocking the calibration fluid from entering the fluid pathway.

2. The fluid sensor module of claim 1, wherein the sensing assembly is coupled to or formed with the housing.

3. The fluid sensor module of claim 1, wherein when the valve is in the sensing position, the sample fluid is conveyed from the fluid inlet, along the fluid pathway, and through the fluid outlet.

4. The fluid sensor module of claim 1, wherein when the valve is in the calibration position, the calibration fluid is conveyed from the calibration fluid reservoir, along the fluid pathway, and through the fluid outlet.

5. The fluid sensor module of claim 4, wherein when the valve is in the calibration position, the sample fluid is conveyed from the fluid inlet to the fluid outlet so as to bypass the fluid pathway.

6. The fluid sensor module of claim 1, wherein the valve has a fill position in which the fluid inlet is directly connected to the calibration fluid reservoir to transfer the calibration fluid from an external source to the calibration fluid reservoir.

7. The fluid sensor module of claim 1, wherein when the valve is in the sensing position, a portion of the sample fluid flows directly between the fluid inlet and the fluid outlet so as to bypass the fluid pathway.

8. The fluid sensor module of claim 1, wherein when the valve is in the sensing position, an entirety of the sample fluid flows along the fluid pathway.

9. The fluid sensor module of claim 1, further comprising a plunger coupled to the housing in the calibration fluid reservoir, the plunger movable to drive the calibration fluid along a calibration fluid pathway to the valve.

10. The fluid sensor module of claim 1, wherein the sensing assembly comprises a functionalized electrode configured to, in response to interacting with the sample fluid, transmit a signal indicative of a constituent component of the sample fluid.

11. The fluid sensor module of claim 1, further comprising a reader, the fluid sensor module configured to electrically and mechanically connect to the reader.

12. A fluid sensor module comprising:
   a sensing assembly;
   a housing;
   a fluid pathway configured to transfer a sample fluid to be in fluid communication with the sensing assembly;

a valve movable between a sensing position in which the sample fluid is transferred along the fluid pathway and a calibration position in which a calibration fluid is transferred from a calibration fluid reservoir along the fluid pathway;

a fluid inlet to transfer the sample fluid into the housing; and a fluid outlet to transfer the sample fluid out of the housing;

wherein when the valve is in the calibration position, the calibration fluid is conveyed from the calibration fluid reservoir, along the fluid pathway, and through the fluid outlet; and wherein when the valve is in the calibration position, the sample fluid is conveyed from the fluid inlet to the fluid outlet so as to bypass the fluid pathway.

13. The fluid sensor module of claim 12, wherein when the valve is in the sensing position, the sample fluid is conveyed from the fluid inlet, along the fluid pathway, and through the fluid outlet.

14. The fluid sensor module of claim 12, wherein the valve has a fill position in which the fluid inlet is directly connected to the calibration fluid reservoir to transfer the calibration fluid from an external source to the calibration fluid reservoir.

15. The fluid sensor module of claim 12, further comprising a plunger coupled to the housing in the calibration fluid reservoir, the plunger movable to drive the calibration fluid along a calibration fluid pathway to the valve.

16. A fluid sensor module comprising:
a sensing assembly;
a housing;
a fluid pathway configured to transfer a sample fluid to be in fluid communication with the sensing assembly;
a valve movable between a sensing position in which the sample fluid is transferred along the fluid pathway and a calibration position in which a calibration fluid is transferred from a calibration fluid reservoir along the fluid pathway;
a fluid inlet to transfer the sample fluid into the housing; and
a fluid outlet to transfer the sample fluid out of the housing;
wherein when the valve is in the sensing position, a portion of the sample fluid flows directly between the fluid inlet and the fluid outlet so as to bypass the fluid pathway.

17. The fluid sensor module of claim 16, wherein the sensing assembly comprises a functionalized electrode configured to, in response to interacting with the sample fluid, transmit a signal indicative of a constituent component of the sample fluid.

18. The fluid sensor module of claim 16, further comprising a reader, the fluid sensor module configured to electrically and mechanically connect to the reader.

19. The fluid sensor module of claim 16, wherein the valve has a fill position in which the fluid inlet is directly connected to the calibration fluid reservoir to transfer the calibration fluid from an external source to the calibration fluid reservoir.

20. The fluid sensor module of claim 16, wherein when the valve is in the sensing position, the sample fluid is conveyed from the fluid inlet, along the fluid pathway, and through the fluid outlet.

* * * * *